(12) United States Patent
Hunter et al.

(10) Patent No.: US 9,681,798 B2
(45) Date of Patent: Jun. 20, 2017

(54) METHODS, SYSTEMS, AND APPARATUS FOR IMAGING SPECTROSCOPY

(71) Applicants: Ian W. Hunter, Lincoln, MA (US); Yi Chen, St. Charles, MO (US)

(72) Inventors: Ian W. Hunter, Lincoln, MA (US); Yi Chen, St. Charles, MO (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 14/933,666

(22) Filed: Nov. 5, 2015

(65) Prior Publication Data

US 2016/0066775 A1 Mar. 10, 2016

Related U.S. Application Data

(63) Continuation of application No. PCT/US2014/038930, filed on May 21, 2014.
(Continued)

(51) Int. Cl.
*A61B 1/06* (2006.01)
*G01J 3/45* (2006.01)
(Continued)

(52) U.S. Cl.
CPC .......... *A61B 1/0638* (2013.01); *G01J 3/0286* (2013.01); *G01J 3/0291* (2013.01); *G01J 3/1256* (2013.01);
(Continued)

(58) Field of Classification Search
CPC .......... A61B 1/0638; G01J 3/2823; G01J 3/45
See application file for complete search history.

(56) References Cited

U.S. PATENT DOCUMENTS

| | | | |
|---|---|---|---|
| 5,162,872 A | * | 11/1992 | Vanasse .................... G01J 3/26 356/519 |
| 5,539,517 A | | 7/1996 | Cabib et al. |

(Continued)

FOREIGN PATENT DOCUMENTS

| | | |
|---|---|---|
| EP | 1484575 A1 | 12/2004 |
| WO | WO 02/14782 A1 | 2/2002 |
| WO | WO 2011/086357 A1 | 7/2011 |

OTHER PUBLICATIONS

Li et al. "Tests of a practical visible-NIR imaging Fourier transform spectrometer for biological and chemical fluorescence emission measurements" Nov. 9, 2009 / vol. 17, No. 23 / Optics Express 21083.*
(Continued)

*Primary Examiner* — Kara E Geisel
*Assistant Examiner* — Dominic J Bologna
(74) *Attorney, Agent, or Firm* — Cooley LLP

(57) ABSTRACT

Imaging spectrometers can be used to generate hyperspectral images for medical diagnoses, contaminant detection, and food safety inspections, among other applications. An exemplary imaging spectrometer includes an integrated position sensing array that measures the relative positions of the interferometer components based on an interference pattern generated by illuminating the interferometer with a reference beam. Such an imaging spectrometer includes a processor that controls the interferometer component position by actuating a voice coil and several piezo-electric elements to align the components with respect to each other and to provide a desired optical path length mismatch between the interferometer arms. In some cases, the processor may use feedback and feed forward control, possibly based on the actuators' transfer functions, for more precise positioning. The processor may also implement adaptive and recursive spectral sampling to reduce the image acquisition period.

27 Claims, 28 Drawing Sheets

Related U.S. Application Data

(60) Provisional application No. 61/826,070, filed on May 22, 2013.

(51) Int. Cl.
    *G01J 3/28*     (2006.01)
    *G01J 3/02*     (2006.01)
    *G01J 3/12*     (2006.01)
    *G01J 3/453*    (2006.01)

(52) U.S. Cl.
    CPC ............... *G01J 3/2823* (2013.01); *G01J 3/45* (2013.01); *G01J 3/453* (2013.01); *G01J 3/4535* (2013.01)

(56) References Cited

U.S. PATENT DOCUMENTS

| | | | |
|---|---|---|---|
| 5,657,122 | A | 8/1997 | Curbelo et al. |
| 5,825,493 | A | 10/1998 | McGlynn |
| 6,005,664 | A | 12/1999 | Korenberg et al. |
| 6,501,551 | B1 * | 12/2002 | Tearney ............ A61B 1/00096 356/477 |
| 6,580,509 | B1 * | 6/2003 | Hutchin .................. G01J 3/453 356/305 |
| 7,092,101 | B2 | 8/2006 | Brady et al. |
| 7,359,058 | B2 | 4/2008 | Kranz et al. |
| 7,518,728 | B2 | 4/2009 | Koo |
| 7,710,574 | B2 | 5/2010 | Sin et al. |
| 7,916,303 | B2 | 3/2011 | Ronnekleiv et al. |
| 8,203,715 | B2 | 6/2012 | Robinson |
| 2003/0016901 | A1 * | 1/2003 | Cormack ............ G01J 3/0218 385/15 |
| 2003/0202186 | A1 * | 10/2003 | Chan ...................... G01J 3/453 356/451 |
| 2004/0201853 | A1 | 10/2004 | Hill |
| 2005/0275847 | A1 | 12/2005 | Moshe |
| 2005/0275848 | A1 | 12/2005 | Hill |
| 2006/0238773 | A1 | 10/2006 | Wellstead et al. |
| 2007/0013916 | A1 | 1/2007 | Kim et al. |
| 2012/0105844 | A1 | 5/2012 | Brady et al. |

OTHER PUBLICATIONS

Boer, G. et al., "Compact static Fourier transform spectrometer with a large field of view based on liquid-crystal technology", Applied Optics, vol. 41, No. 7, (Mar. 1, 2002), pp. 1401-1407.
Brady, D. J. et al., "Compressive sampling strategies for integrated Microspectrometers", Intelligent Integrated Microsystems, Proc. of SPIE, vol. 6232, (2006), 9 pages.
Chao, T.H. et al., "Electro-Optic Imaging Fourier Transform Spectrometer", Defense and Security, International Society for Optics and Photonics, (2005), 6 pages.
De Groot, P et al. "Three-dimensional imaging by sub-Nyquist sampling of white-light interferograms", Optics Letters, vol. 18, No. 17 (1993), pp. 1462-1464.
Do, T. T. et al., "Sparsity Adaptive Matching Pursuit Algorithm for Practical Compressed Sensing", Signals, Systems and Computers, 2008 42$^{nd}$ Asilomar Conference on IEEE, (2008), 7 pages.
Feng, P. et al., "Spectrum-Blind Minimum-Rate Sampling and Reconstruction of Multiband Signals", "Spectrum-blind minimum-rate sampling and reconstruction of multiband signals." Acoustics, Speech, and Signal Processing, 1996. ICASSP-96. Conference Proceedings, 1996 IEEE International Conference on. vol. 3. IEEE, (1996), pp. 1688-1691.
Foster, B. et al., "Exact Reconstruction from Periodic Nonuniform Samples", Acoustics, Speech, and Signal Processing, 1995. ICASSP-95., 1995 International Conference on. vol. 2. IEEE, (1995), pp. 1452-1455.
Gehm, M. E. et al., "Adaptive spectroscopy: Towards adaptive spectral imaging", SPIE Defense and Security Symposium. International Society for Optics and Photonics, (2008), 11 pages.
Gregorcic, P. et al., "Quadrature phase-shift error analysis using a homodyne laser interferometer," Optics Express, vol. 18, No. 17, (2009): 16322-16331.
Heintzmann, K. A. Lidke et al., "Double-pass Fourier transform imaging spectroscopy", Optics Express, vol. 12, No. 5, Mar. 8, 2004, pp. 753-763.
Hong, S., "Direct Spectrum Sensing from compressed measurements", Military Communications Conference, Stanford University, 2010-MILCOM, IEEE, (2010), 6 pages.
Katz, O. et al., "Compressive Fourier transform spectroscopy" Frontiers in Optics, Optical Society of America, (2010), 5 pages.
Kinast, J. et al., "Adaptive dynamic range matching for spectroscopic measurements", Applied Optics, vol. 48, No. 10, Apr. 1, 2009, pp. 1891-1897.
Korenberg, M. J., "A Robust Orthogonal Algorithm for System Identification and Time-Series Analysis", Biological Cybernetics, vol. 60, (1989), pp. 267-276.
Korenberg, M. J. et al., "Raman Spectral Estimation via Fast Orthogonal Search", Analyst, vol. 122, (1997), pp. 879-882.
Kudenov, M. W. et al., "Compact snapshot birefringent imaging Fourier transform spectrometer", SPIE Optical Engineering+ Applications. International Society for Optics and Photonics, (2010), 11 pages.
Manzardo, O. et al., "Miniaturized time-scanning Fourier transform spectrometer based on silicon technology", Symposium on Micromachining and Microfabrication. International Society for Optics and Photonics, vol. 24, No. 23, (1999), pp. 1705-1707.
Peck, E. R. et al., "Wavelength or Length Measurement by Reversible Fringe Counting", Journal of the Optical Society of America, vol. 43, No. 6., (Jun. 1953), pp. 505-509.
Solf, C. et al., "Miniaturized LIGA Fourier Transformation Spectrometer", Sensors, 2003. Proceedings of IEEE. vol. 2. IEEE, (2003), 4 pages.
Sun, H. et al., "Adaptive compressive spectrum sensing for wideband cognitive radios" Communications Letters, IEEE, vol. 16, No. 11, (2012), pp. 1812-1815.
Venema, S. C., "A Kalman Filter Calibration Method for Analog Quadrature Position Encoders", Diss. University of Washington, (1994), 99 pages.
Volin, C. E., et al., "High-speed spectral imager of imaging transient fluorescence phenomena", Applied Optics, vol. 37, No. 34, Dec. 1, 1998, pp. 8112-8119.
Wadsworth, W. et al., "Rugged high speed rotary imaging Fourier Transform Spectrometer for industrial use", Environmental and Industrial Sensing. International Society for Optics and Photonics, (2002), 6 pages.
Wu, L. et al., "A Miniature Fourier Transform Spectrometer by a Large-Vertical-Displacement Microelectromechanical Mirror", Fourier Transform Spectroscopy. Optical Society of America, (2009), 3 pages.
Zhang, H. et al., "Imaging Fourier transform endospectroscopy for in vivo and in situ multispectral imaging", Optics Express, vol. 20, No. 21, (2012), pp. 23349-23360.
Zhao, J. et al., "Multichannel Fourier Transform Raman spectroscopy: Cornbining the Advantages of CCDs with Interferometry." Applied Spectroscopy, vol. 50, No. 9, (1996), pp. 1209-1214.
International Search Report and the Written Opinion of the International Searching Authority, or the Declaration in related PCT Application No. PCT/US2014/38930, filed May 21, 2014, mailed Sep. 24, 2014, 11 pages.
International Search Report on Patentability and Written Opinion of the International Searching Authority in related PCT Application No. PCT/US2014/38930, filed May 21, 2014, mailed Dec. 3, 2015, 9 pages.

* cited by examiner

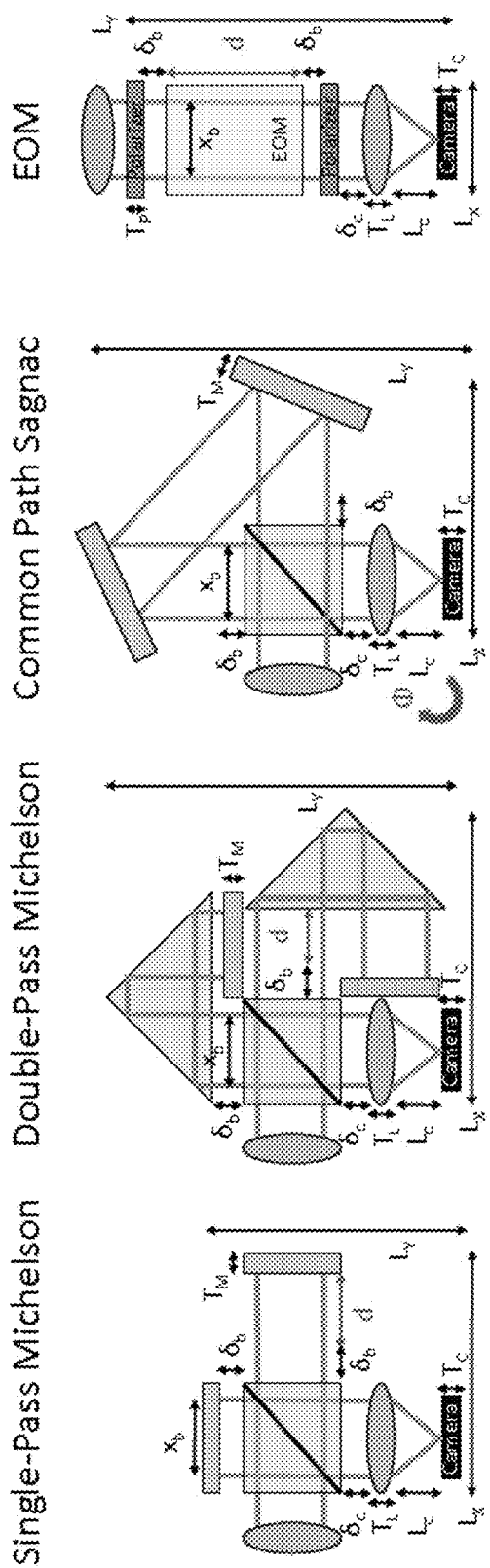

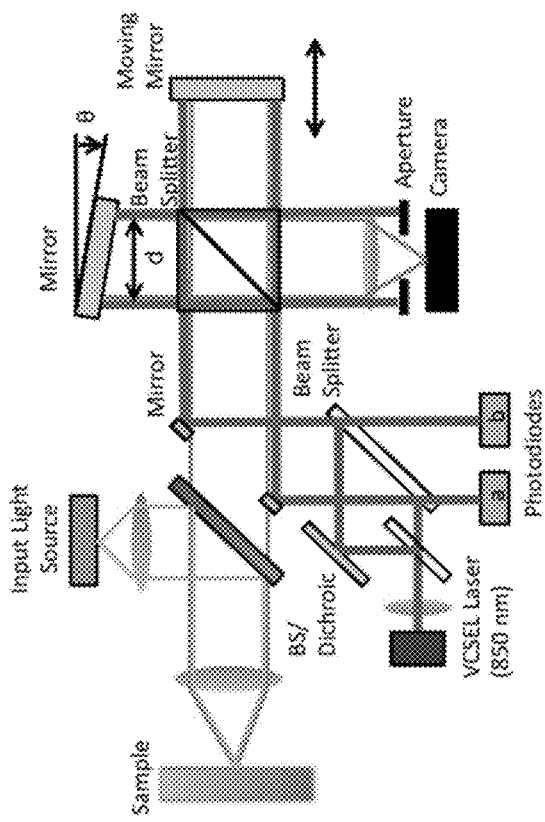
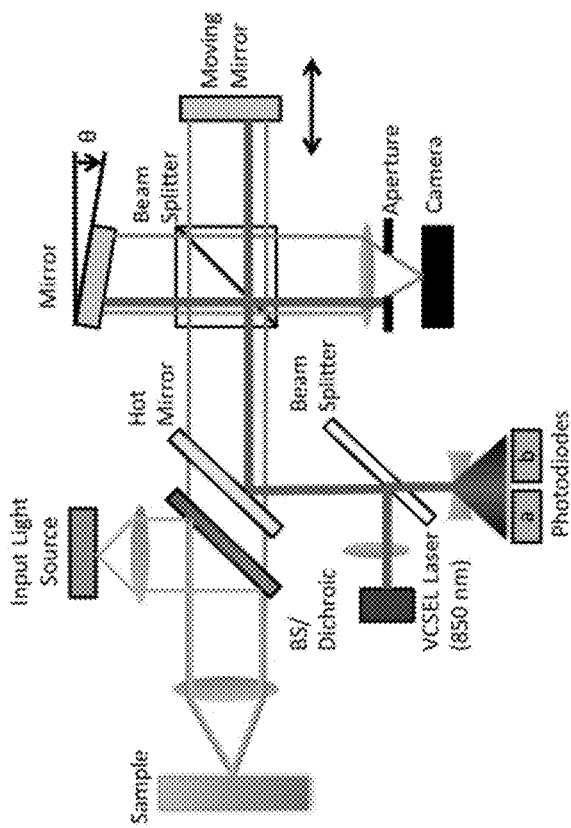
FIG. 2B
FIG. 2A

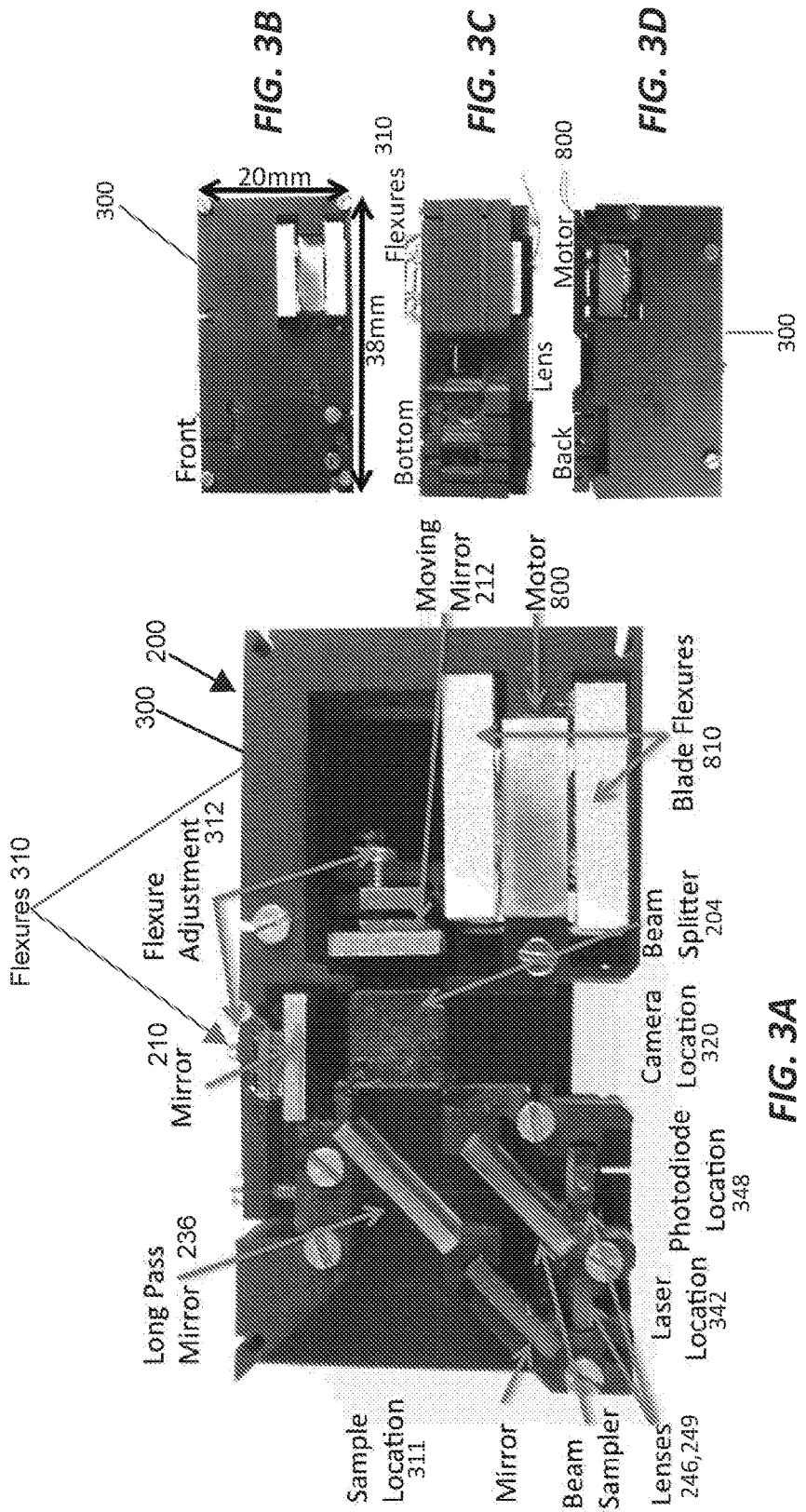

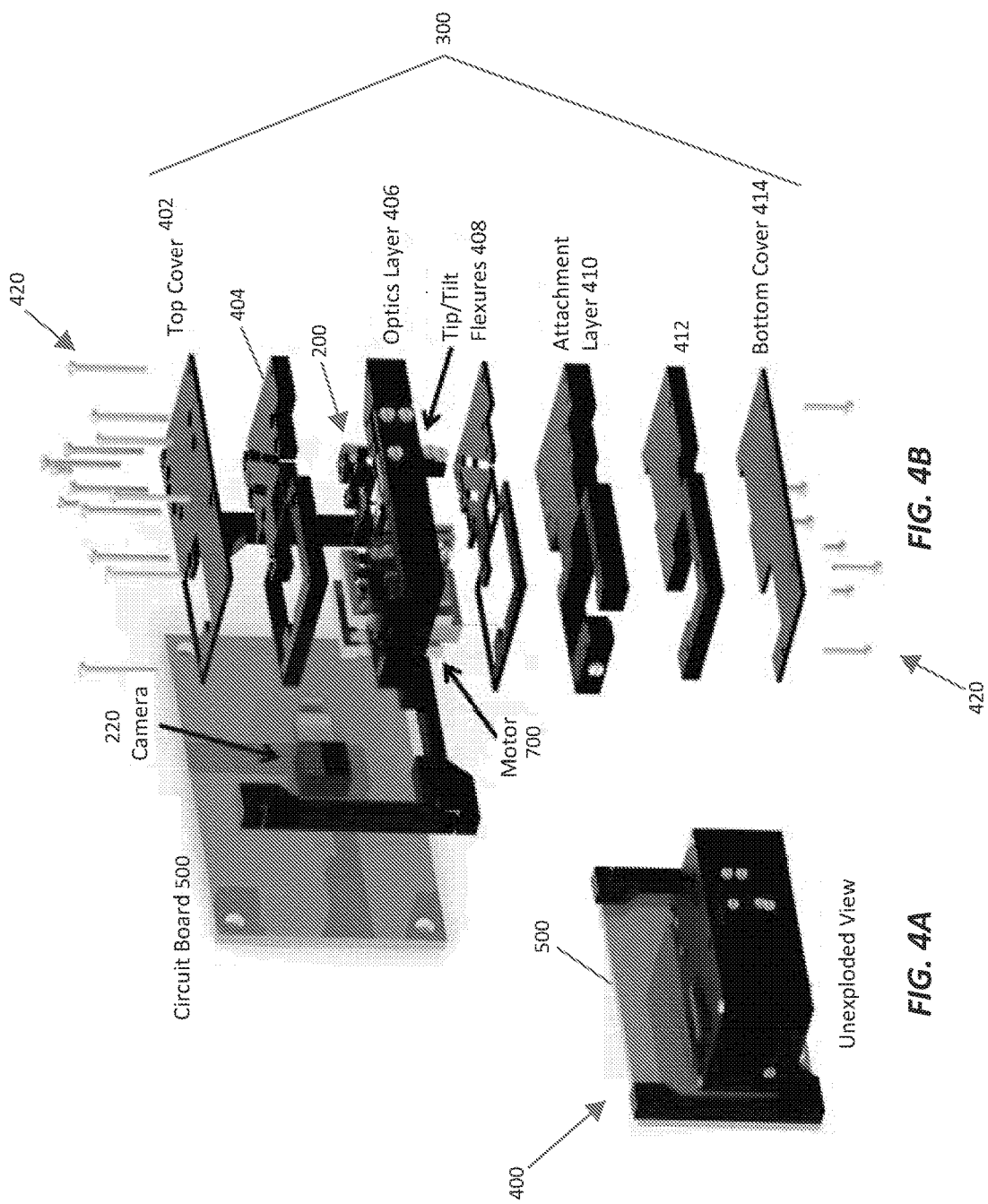

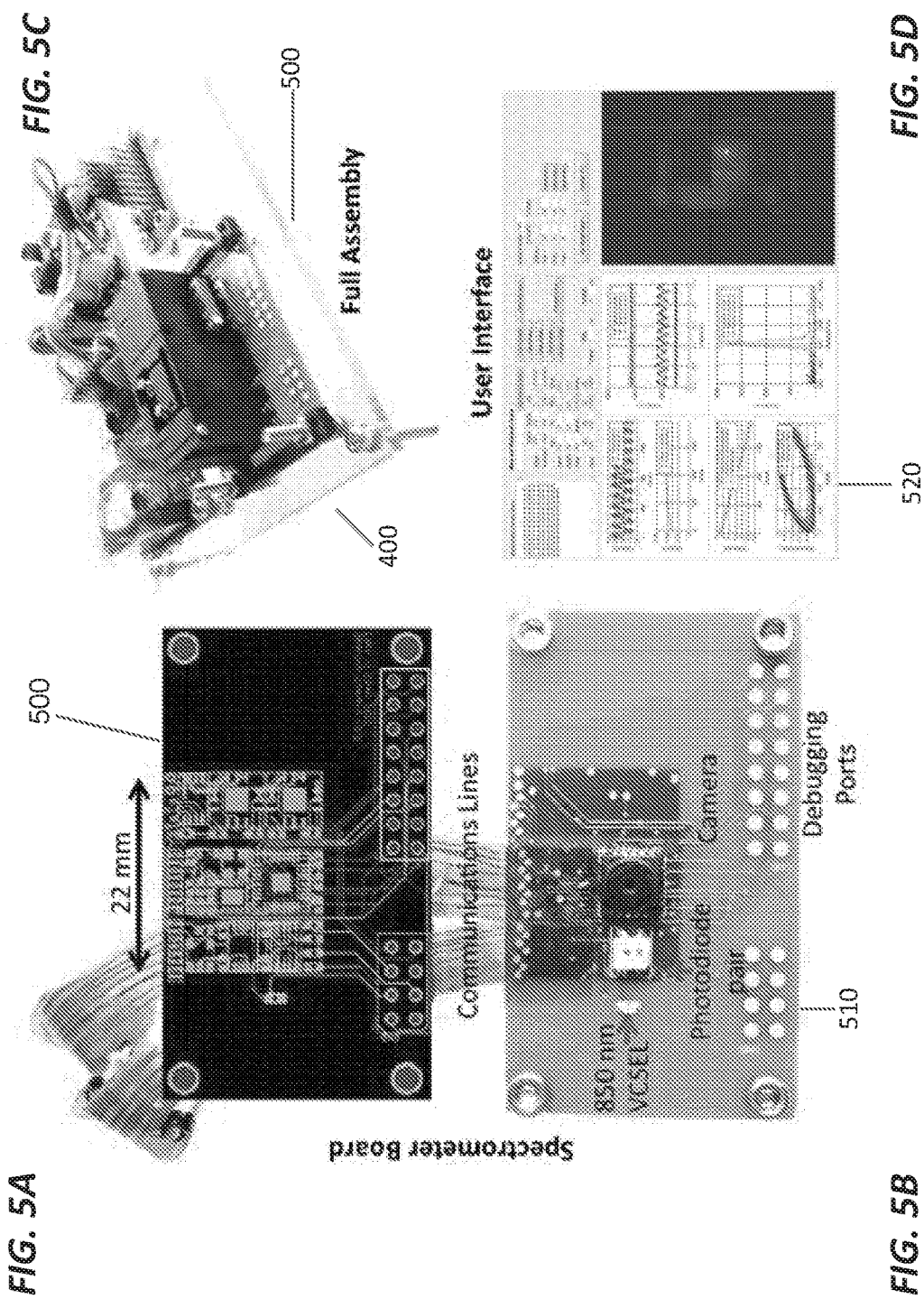

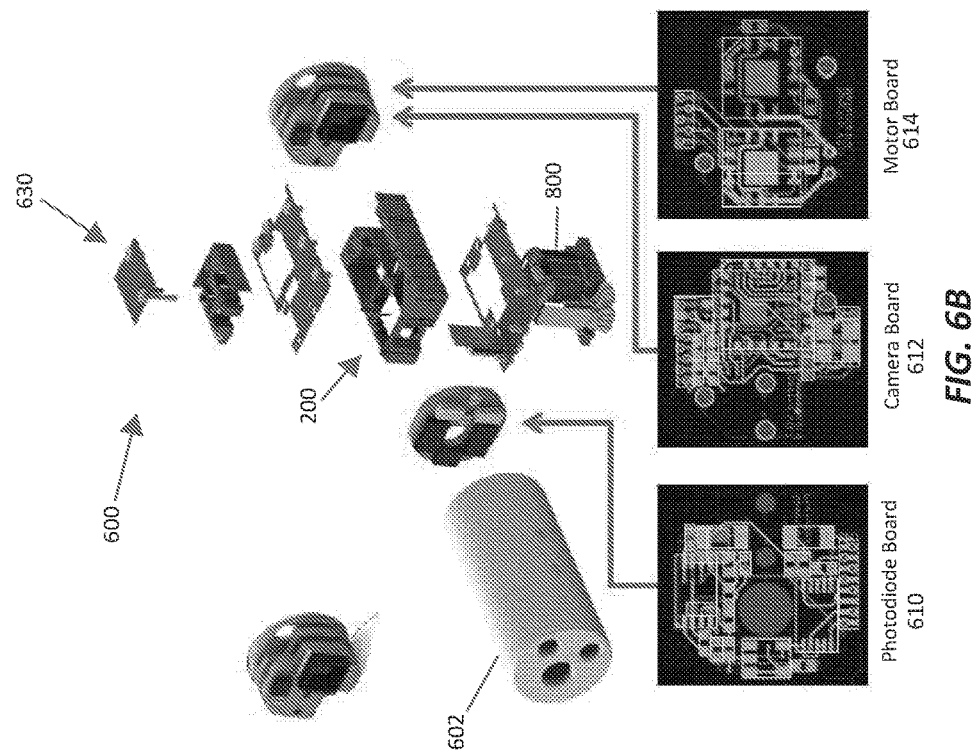
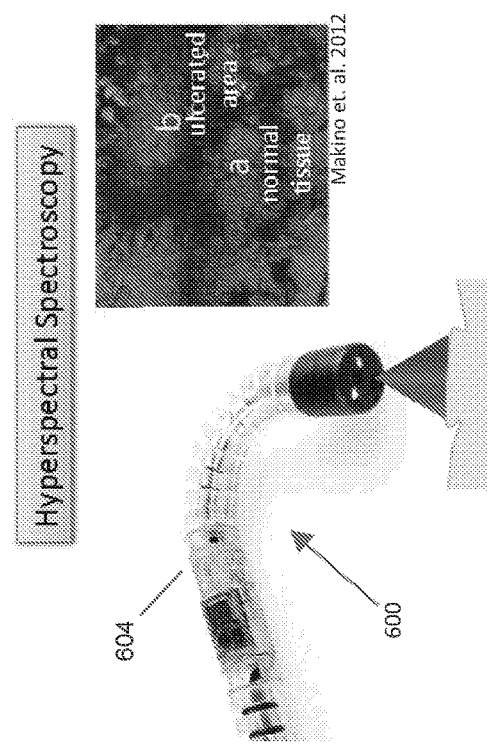
FIG. 6A
FIG. 6B

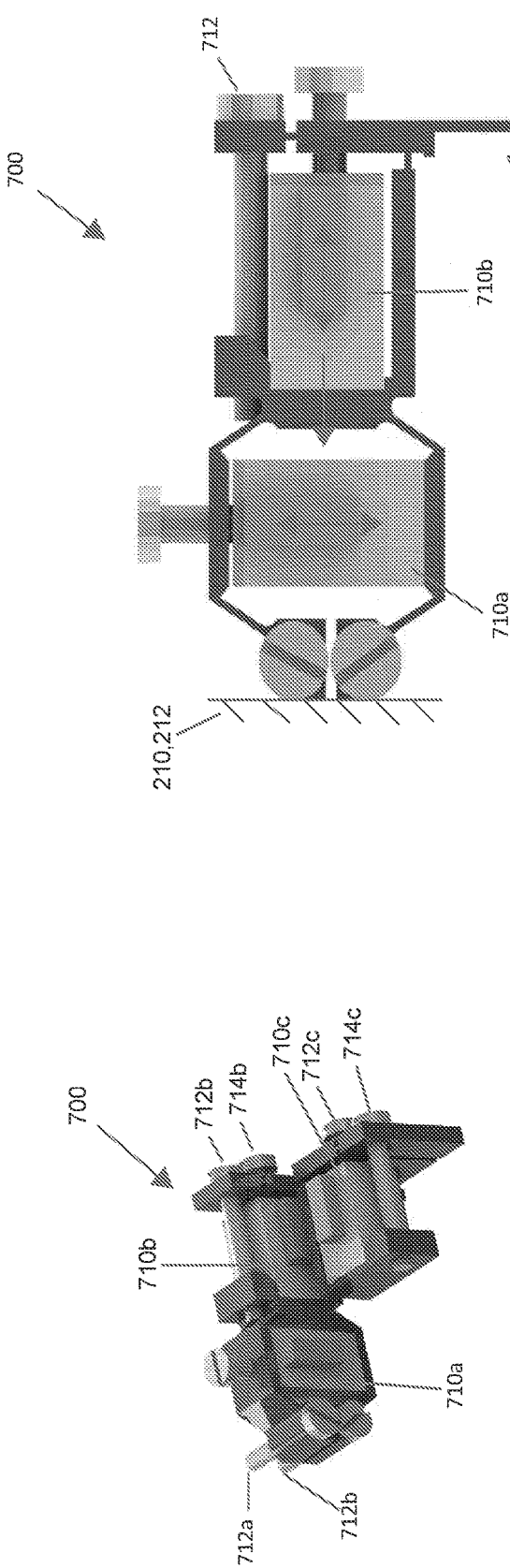
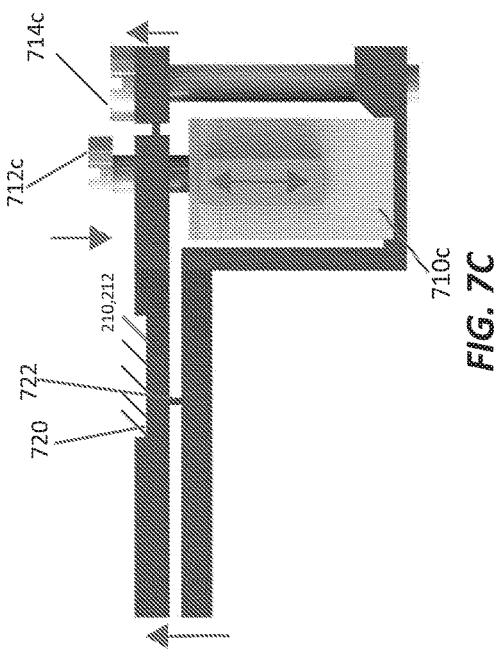
FIG. 7B
FIG. 7C
FIG. 7A

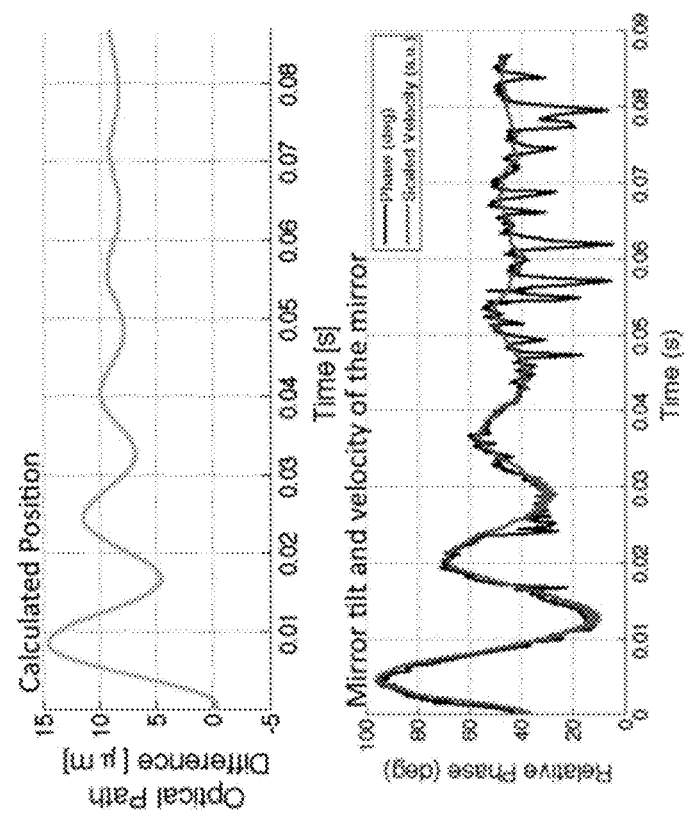
FIG. 10C
FIG. 10D
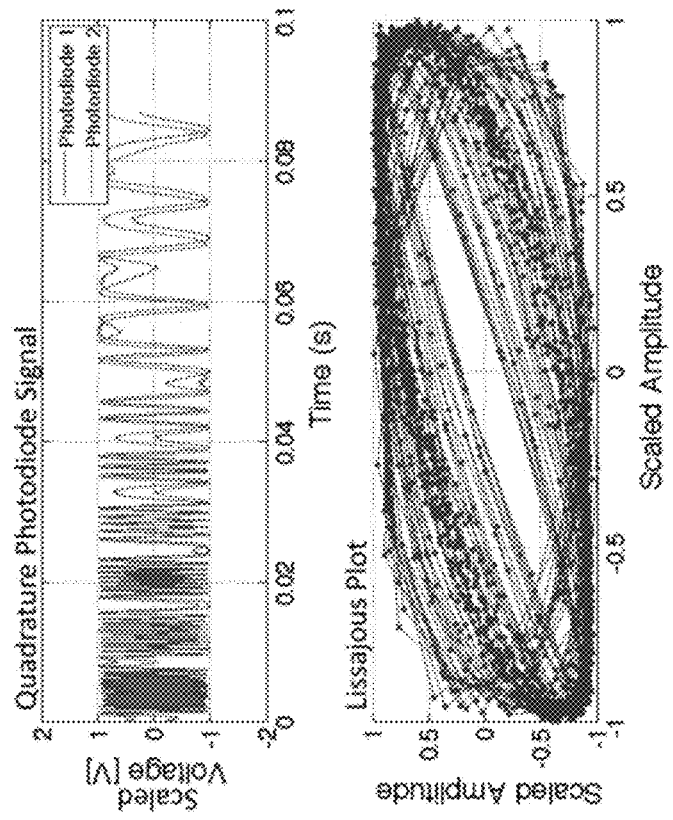
FIG. 10A
FIG. 10B

Simple Feed Forward

Full Model Inversion Feed Forward

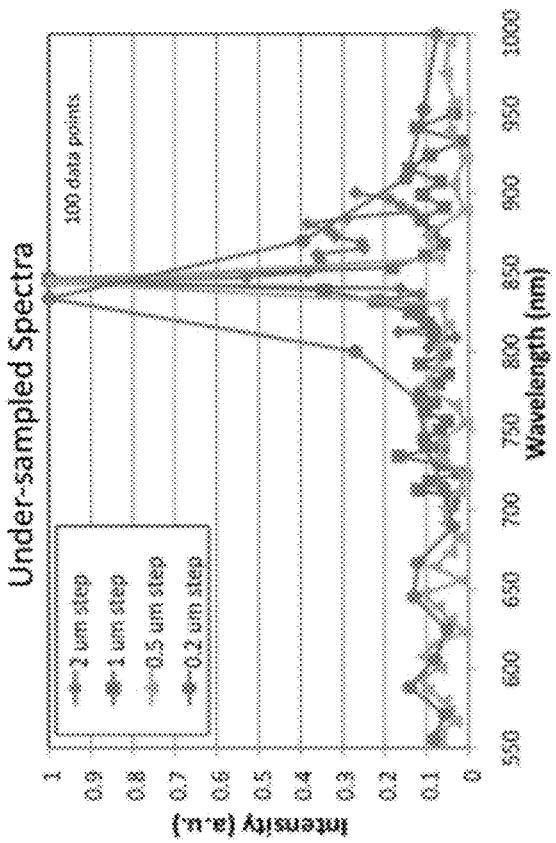
FIG. 22B
FIG. 22A
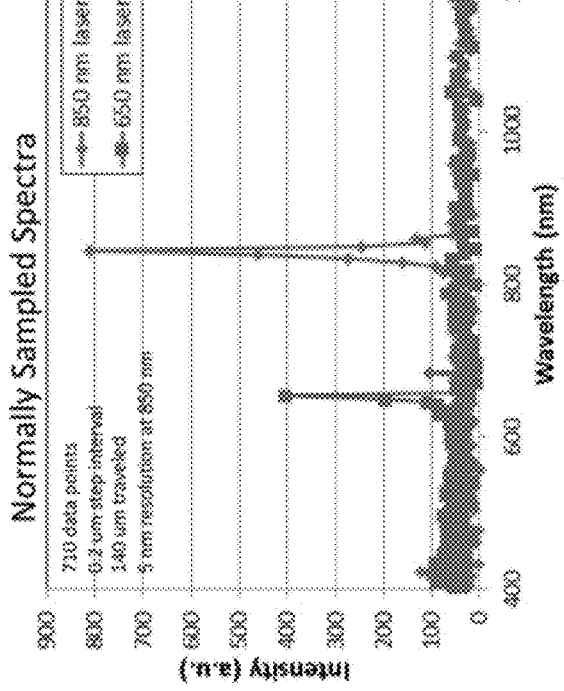
FIG. 22C

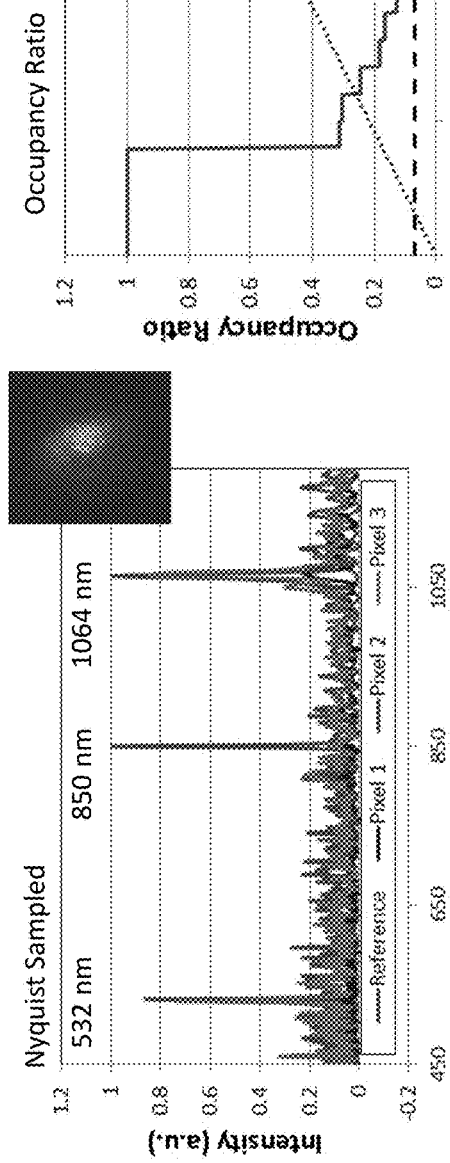
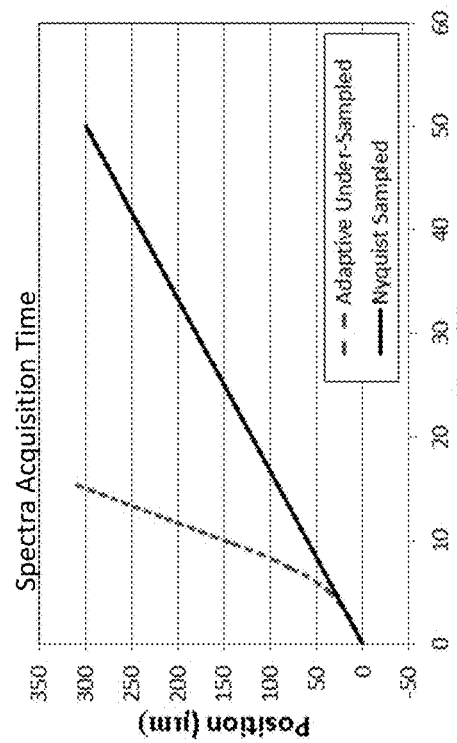
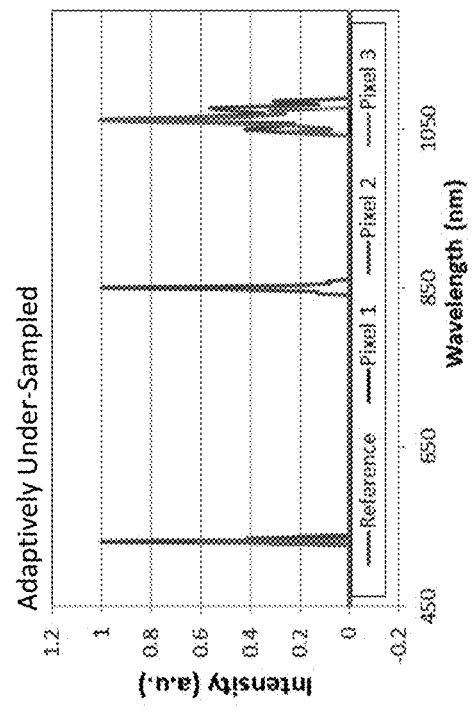
FIG. 25A
FIG. 25B
FIG. 25C
FIG. 25D

METHODS, SYSTEMS, AND APPARATUS FOR IMAGING SPECTROSCOPY

CROSS-REFERENCE TO RELATED PATENT APPLICATION

This application is a continuation of PCT Application No. PCT/US2014/038930, filed May 21, 2014, and entitled "Design and Mathematical Methods for a Fast Miniature Hyperspectral Imaging Transform Spectrometer," which claims priority, under 35 U.S.C. §119(e), from U.S. Application No. 61/826,070, filed May 22, 2013, and entitled "Design and Mathematical Methods for a Fast Miniature Hyperspectral Imaging Transform Spectrometer." Each of the above-reference applications is hereby incorporated herein by reference in its entirety.

BACKGROUND

An imaging spectrometer is a device that takes images that include information about the different wavelengths of light. When this device is combined with specialized types of input light, such as fluorescence or Raman inputs, it can be used to differentiate between different materials that are indistinguishable to the naked eye in a nondestructive manner. An imaging spectrometer takes many spectral data points from an image at the same time, also making it easier to align to a target.

Many small spectrometers contain imaging sensors but are not imaging spectrometers. Most of these small spectrometers contain dispersive elements or conduct line-based Fourier transforms so they measure the spectra of a single pixel or a limited number of pixel much smaller than the number of points on the imaging sensor. They can only take an image if raster scanned. Dispersive methods do not take advantage of spectral multiplexing and cannot take advantage of the irregular sampling techniques outlined in this work. There are also miniature Fourier transform spectrometers that are single-point spectrometers, which do not perform direct imaging.

SUMMARY

The inventors have recognized that miniaturizing an imaging spectrometer would make it possible to perform hyperspectral imaging in a wide variety of settings. These settings include but are not limited to colonoscopies to search for cancerous polyps, cancer margin detection, handheld personal diagnostics (e.g., to detect blood analyte levels, such as blood oxygen levels, glucose levels, triglyceride levels, etc., or for skin cancer detection and analysis of diseases), handheld food safety checks, quality checks and characterization (e.g., to measure the purity of materials such as diamonds, crystalline materials, alloys, plastics, chemical compounds, etc.), and pollution (such as air quality) and contaminant monitoring. An exemplary spectrometer may operate over a variety of wavelengths including but not limited to ultraviolet (UV), visible, near infrared (IR), and IR. An exemplary device can also be used in areas including but not limited to FTIR (Fourier transform infrared) spectroscopy, white light interferometery and optical coherence tomography.

Embodiments of the present invention include systems and methods for imaging spectroscopy of an object that emits, reflects, or scatters light. In one example, the system includes an interferometer in optical communication with the object and first and second detector arrays and a reference light source in optical communication with the interferometer. In operation, the interferometer delays a first portion of an object beam from the object with respect to a second portion of the object beam by a delay period. This delay period is proportional to a optical path length difference defined by a first optical element and a second optical element in the interferometer. The first detector array senses at least one object interference pattern between the first portion of the object beam and the second portion of the object beam; this object interference pattern represents a spectroscopic image of at least a portion of the object. The reference beam light source illuminates the first optical element with a first portion of a reference beam and the second optical element with a second portion of the reference beam. And the second detector array senses a reference interference pattern between the first portion of the reference beam and the second portion of the reference beam. This reference interference pattern representing a relative position, tip or tilt of the first optical element with respect to the second optical element.

Other embodiments of the present invention include an imaging spectrometer that comprises a beamsplitter, at least one optical element, in optical communication with the beamsplitter, at least one actuator mechanically coupled to the optical element, a detector array in optical communication with the optical element, and a processor coupled to the detector array. In operation, the beamsplitter splits light from an object into a first object beam and a second object beam. The optical element delays the first object beam with respect to the second object beam by a plurality of delay periods. The actuator moves the optical element to each of a plurality of positions so as to produce the plurality of delay periods. The detector array senses a plurality of interference periods, each of which includes at least one interference pattern between the first object beam and the second object beam at each delay period in the plurality of delay periods. And the processor determines a spectroscopic image of the object based at least in part on the plurality of interference patterns and to determine at least one position in the plurality of positions based at least in part on the spectroscopic image and a transfer function of the actuator.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1A-1D show different interferometer configurations for compact hyperspectral imaging spectrometers.

FIG. 2A illustrates a hyperspectral imaging spectrometer with photodetectors to sense the relative positions of a pair of mirrors in a Michelson interferometer.

FIG. 2B illustrates another hyperspectral imaging spectrometer with photodetectors to sense the relative positions of a pair of mirrors in a Michelson interferometer.

FIGS. 3A-3D show different views of a compact hyperspectral imaging spectrometer.

FIGS. 4A and 4B show an unexploded view and an exploded view, respectively, of the compact hyperspectral imaging spectrometer of FIGS. 3A-3D.

FIGS. 5A-5D show electronics and a user interface of the compact hyperspectral imaging spectrometer of FIGS. 3A-3D.

FIG. 6A shows an endoscopic hyperspectral imaging spectrometer at the bending tip of an endoscope.

FIG. 6B shows an exploded view of the endoscopic hyperspectral imaging spectrometer of FIG. 6A.

FIGS. 7A-7C show different views of a piezo-electric tip/tilt/translation actuator for a compact hyperspectral imaging spectrometer.

FIG. 10A is a plot of photodetector signals versus time for a pair of sensors measuring the position of one mirror with respect to another mirror in different arms of an interferometer.

FIG. 10B is a Lissajous plot of photodetector signals shown in FIG. 10A.

FIGS. 10C and 10D are plots of calculated and measured mirror position and mirror velocity plotted against the relative phase of the two signals for the measurement of FIGS. 10A and 10B.

FIGS. 22A-22C illustrate the performance of under-sampling versus normal (Nyquist) sampling with an exemplary imaging spectrometer.

FIGS. 25A-25D are plots illustrating the performance of adaptive sampling versus Nyquist sampling with an exemplary imaging spectrometer.

DETAILED DESCRIPTION

Figures 8A, 8B, 8C, 8D:
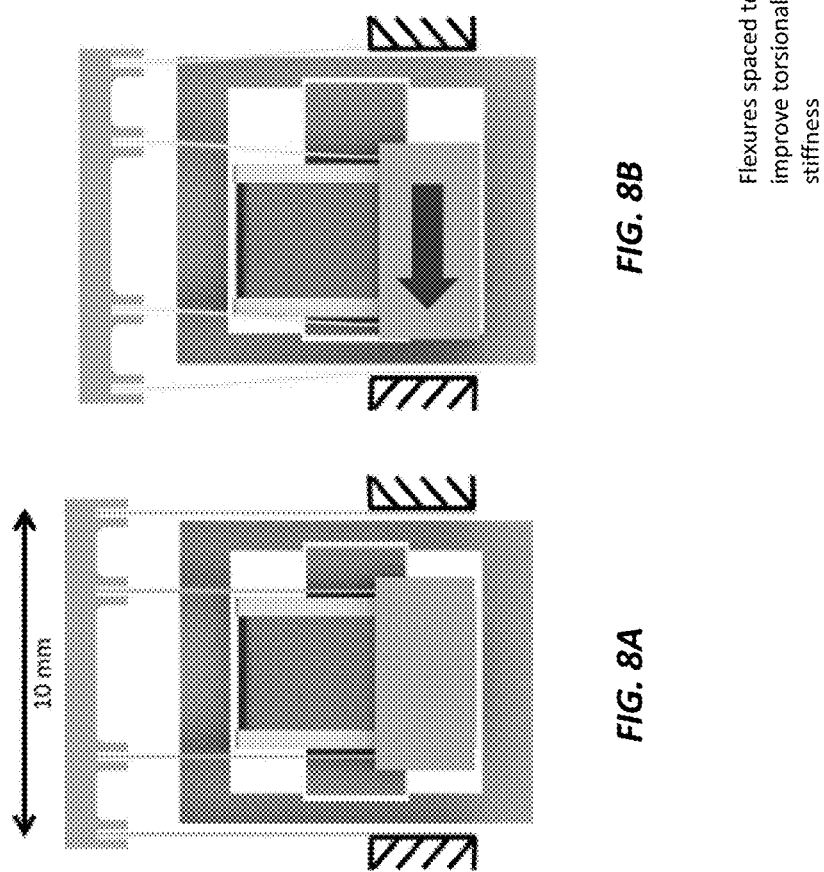
FIGS. 8A and 8B show cutaway views of an actuator and a flexure for moving a mirror or other optical element in a compact hyperspectral imaging spectrometer at rest and in an actuated position, respectively.
FIG. 8C shows another cutaway view of an actuator and a flexure for moving a mirror or other optical element in a compact hyperspectral imaging spectrometer.
FIG. 8D shows a perspective view of an actuator and a flexure for moving a mirror or other optical element in a compact hyperspectral imaging spectrometer.

Non-invasive diagnostics using small spectrometers have many applications in medicine and biology. A small, fast, and high spectral resolution imaging system can be applied to many areas including the analysis of the concentration of blood analytes and the optical biopsy of tissues to test for colon cancer. A portable device can be used for measurements in the field or used for personal diagnostics. A miniature portable imaging spectrometer has many other applications outside of biology including environmental science, process monitoring, and security.

For example, a portable, imaging Fourier-transform spectrometer can be used for absorption, fluorescence, Raman, and Coherent Raman Scattering (CARS) spectroscopy. Such a spectrometer can be small enough to fit in the palm of the hand or at the end of an endoscope (e.g., a colonoscope with a diameter of about 10 mm to about 15 mm) It can operate in several spectral analysis modes (e.g., with spectral resolutions of 1.6 cm$^{-1}$ to 70 cm$^{-1}$) and can produce continuous video, making it easier for users to align and focus the instrument to a desired location.

To provide stable handheld operation, an exemplary device may use an active position measurement system, a high-speed actuator, and a control system to stabilize internal scanning mirrors and/or other moving components. For instance, it may include small linear Lorentz-force actuators, piezoelectric actuators, flexures, precise position measurement systems (e.g., with precision of 30 nm or better), and external disturbance rejection control systems. And it may include an optomechanical mounting system and frame made using layers of metals made through electric discharge machining.

Like other transform spectrometers, including conventional Fourier-transform spectrometers, an exemplary transform spectrometer takes several data points at different autocorrelations of input light and then reconstructs the spectral data. Compared to conventional transform spectrometers, however, the transform spectrometers disclosed herein can obtain spectral data relatively quickly using adaptive and recursive techniques. For instance, an exemplary spectrometer can reconstruct a given set of spectral information with as few as 8-10% of the number of images used by a conventional Fourier-transform spectrometer. Thus, an exemplary spectrometer may operate about ten times faster than a conventional Fourier-transform spectrometer.

An exemplary spectrometer's size and data acquisition speed makes it suitable for applications from medical imaging to security to process monitoring. In medicine, a small imaging spectrometer can be used on the tip of an endoscope for identifying cancerous polyps. It can also be used to detect cancer margins during surgery in cramped surgical environments. A small imaging spectrometer would be easy to align and carry around and can be used by consumers for personal diagnostics of skin cancer, blood analyte levels (e.g., glucose levels, cholesterol levels, etc.), and other common conditions.

An exemplary device can also be used for process monitoring to check the freshness of fruits and vegetables, to check composition of materials on the manufacturing line, to scan for lead paint, etc. A small device can be embedded into the manufacturing line easily or can be held by personnel for monitoring. An imaging spectrometer can be easier to align to a specific target, making it possible to monitor multiple points at the same time. This type of device can also be used in security applications such as screening for hazardous substances in the air, pollution monitoring, monitoring agriculture, or for screening letters and packages. For instance, an exemplary device may be mounted on an aircraft or drone for crop monitoring and localized pesticide/herbicide distribution, or on robots for investigating hazardous environments (e.g., contaminated, high-pressure, and extremely hot or cold environments).

1.0 Interferometer Layouts and Optomechanical Mounting

There are several possible designs for an imaging spectrometer. One desirable quality is to have access to the full image so that the spectrometer can be turned off for regular imaging, which reduces the computational load and the power consumption. For certain applications, including endoscopy, the ability to switch between regular imaging and hyperspectral imaging makes it possible to align the spectrometer with respect to the sample without an additional alignment camera. Being able to select the wavelength resolution on the fly and to obtain high-resolution images is also desirable.

Fourier transform spectrometers offer common path regular/hyperspectral imaging, high resolution, and selectable wavelength resolution. In Fourier transform topology spectrometers, spectral information is multiplexed thereby leading to a high throughput efficiency, which also leads to the possibility of greatly under-sampling the spectra leading to high speeds. Fourier-transform spectrometers can also be miniaturized, e.g., to fit inside handheld packages and endoscopes.

FIGS. 1A-1D show different types of interferometers suitable for use in a Fourier transform spectrometer. FIG. 1A shows a single-pass Michelson interferometer 100 that includes a first lens 102, which projects an incident beam onto a beamsplitter 104. The beamsplitter 104 directs a first portion of the incident beam onto a static mirror 110 and a second portion of the incident beam onto a moving mirror 112. These mirrors 110, 112 reflect the incident light back towards the beamsplitter 104, which directs a recombined beam onto a detector array (camera 120) via a lens 106. In operation, an actuator (not shown) moves the moving mirror 112 back and forth to change the path length difference between the arms of the interferometer 100. The camera 120 detects an image at each mirror position, and a processor coupled to the camera (not shown) combines the individual images into a hyperspectral image of the scene or object.

FIG. 1B shows a double-pass Michelson interferometer 130 that includes a pair of prisms 132 and 134 to increase the path length. As shown in FIG. 1B, the beams split by the beamsplitter 104 reflect off internal faces of the retroreflectors 132, 134 towards the moving mirror 110 and the static mirror 112. FIG. 1C shows a common-path Sagnac interferometer 150 that includes a pair of tilted mirrors 152 and 154. In this case, the beam splitter 104 directs portions of the incident beam onto the tilted mirrors 152 and 154, which reflect light towards each other and back towards the beam splitter. One or both of the tilted mirrors can be rotated and/or translated to vary the path length of the Sagnac interferometer. In addition, the entire Sagnac interferometer can be rotated with respect to the sample to change the optical path length of the light incident on the camera 120. And FIG. 1D shows an electro-optic modulated (EOM) imaging Fourier-transform spectrometer 170 that includes a first polarizer 172, an electro-optic material 174, and a second polarizer 176 arranged in series between the input lens 102 and the camera 120. Applying a voltage to the electro-optic material 174 changes the relative speed difference between the ordinary and extraordinary components of light thereby changing the time delay between the two polarizations of light passing through the modulator. This time delay operates like the spatial delay of the other designs creating an interference pattern as a function of the voltage on the EOM.

A Fourier transform topology with a moving mirror Michelson configuration as shown in FIG. 1A has several advantages over other optical layouts. First, it provides access to the full image so the spectrometer can be turned off for regular imaging (unlike raster-scanning and push-broom systems) and does not put additional interference patterns on the image if properly aligned (which is a problem for Wollaston prism interferometers). The wavelength resolution can be selected on the fly (something that is difficult for coded aperture systems). And the spectral resolution can be extremely high (e.g., higher than common-path Sagnac interferometers and EOM interferometers with the same optical component dimensions). The spectral information is multiplexed thereby leading to a high throughput efficiency (electro-optic imaging Fourier-transform spectroscopy systems have a lower throughput due to polarization elements), which also leads to the ability to greatly under-sample the spectra leading to high speeds. This is a trait that filter-based spectrometers (e.g., Bayer masks, rotating filters, Fabry Perot cavities, acousto-optic systems, and electro-optic systems) and tunable input spectrometers (e.g., light-emitting diodes, lasers, tunable optical parametric oscillators) lack as the spectral information is not mutiplexed. In addition, the system can be miniaturized to the desired handheld and personal phone-size scales unlike many of the other technologies (such as fiber optic systems).

FIGS. 2A and 2B show optical layouts 200 and 201, respectively, for an instrument that uses a Michelson interferometer setup for input image autocorrelation. Each layout 200, 201 includes an input light section 230 for illuminating a sample with a beam 231 of white light or laser light (e.g., for Raman or fluorescence spectroscopy). The input light section 230 includes an input light source 238, such as a laser, light emitting diode (LED), or other source, that emits the beam 231 via a lens 232 towards a dichroic or regular beam splitter 234. The dichroic or regular beam splitter 234 reflects the beam 231 towards another lens 202 which projects light onto a sample 11. The sample 11 reflects or emits light in response to the illumination by the beam 231 from the input light source 230. In some cases, the sample 11 emits light or is illuminated by one or more external light sources, in which case the spectrometer may not include an input light source and related optical components.

The lens 202 images light from the sample 11 onto a camera (detector array) 220 via a lens 206 and a Michelson interferometer formed by a beamsplitter 204, a static mirror 210, and a moving mirror 212. As described above, and an actuator (not shown) translates the moving mirror 212 back and forth to change the optical path length difference between the arms the interferometer. In some cases, the actuator steps the moving mirror 212 through a series of discrete positions, and the camera acquires one frame or image of the sample 11 at each of these positions. A processor (not shown) operably coupled to the camera to 20 combines these flames to form a hyperspectral image of the sample 11 with a spectral resolution as fine as about $1.6 \text{ cm}^{-1}$ for each pixel in the hyperspectral image.

Each layout 200, 201 also includes an respective integrated position sensing system 240, 280. In FIG. 2A, the integrated position sensing system 240 includes a vertical cavity surface emitting laser (VCSEL) 242, which emits a beam 241 of coherent infrared light, e.g., at a wavelength of 850 nm. Other types of compact, long coherence length lasers can also be used for tip, tilt, and translation sensing. For finding or sensing the center of the interferometer (where the distances from the beam splitter 204 to the mirrors 210 and 212 are equal), the spectrometer may include a low coherence length light source, such as a white light, low coherence LED, superluminescent LED, or a thermal emitter. This infrared beam 241 reflects off the beamsplitter 244 towards a hot mirror or dichroic filter 236, which directs the beam 241 into the interferometer. The beamsplitter 244 splits the beam 241 into a first portion propagating towards the static mirror 210 and a second portion propagating towards the moving mirror 212. The mirrors 210, 212 reflect the respective portions of beam 241 back towards the beamsplitter 204, which re-combines the beams portions and directs the recombined beam 241 towards the camera 220. An aperture 208 or beamstop prevents the recombined beam 241 from illuminating the camera 220 and potentially saturating the hyperspectral image.

The beamsplitter 204 also directs the recombined beam 241 back towards the integrated position sensing system 240 via the hot mirror 236. The beamsplitter 244 in the integrated position sensing system 240 directs a portion of the recombined beam 241 towards a set of photodiodes 248, such as a quad photodetector, via a diverging lens 249 and/or other optical elements. The photodiodes 248 detecting interference pattern whose periodicity and orientation is proportional to the misalignment between the static mirror 210 and the moving mirror 212. This interference pattern can be used to generate commands for actuators that control the position of the moving mirror 212 with respect to the static mirror 210 as described in greater detail below.

The integrated position sensing system 280 shown in FIG. 2B also includes a VCEL 242 that emits an infrared beam 241 towards the Michelson interferometer. In this case, however, the integrated position sensing system 280 includes an extra beamsplitter 284 and a set of mirrors 236a-236c (collectively, mirrors 236) that split the beam 241 into different portions, which reflect off different areas of the static mirror 210 and moving mirror 212 to illuminate respective photodetectors 248 as shown in FIG. 2B. As described in greater detail below, the intensity detected by the photodetectors 248 represents the position of the static mirror 210 with respect to the moving mirror 212 and can be used to determine misalignment and actuator commands to correct or compensate for the misalignment.

FIGS. 3A-3D show different views of an optomechanical mounting system 300 for holding the optical components in the interferometers shown in FIGS. 2A and 2B. The optomechanical mounting system 300 includes several layers of electric discharge machined (EDM) aluminum and/or other suitable materials with very small feature sizes (e.g., <30 μm), e.g., as shown in FIGS. 4A and 4B. Other manufacturing methods include but are not limited to high aspect ratio micro-electro-mechanical systems (MEMS), Lithography, Electroplating, and Molding (LIGA), X-ray lithography, micromachining, injection molding, casting, metal extrusion molding, and high-resolution 3D printing. Suitable materials should have the properties of low thermal expansion, high stiffness, and high yield strength to allow for internal flexures. They may not be magnetic as to prevent interference with the operation of the electric motor if an electric motor is used. The features machined in the optomechanical mounting system 300 include cavities, apertures, and mounts for the various optical components, including an aperture 311 for the sample 11, a cavity 320 for the camera 220, a cavity 342 for the position-sensing VCSEL 242, and a cavity 348 for the position-sensing photodetector array 248. The optomechanical mounting system 300 also defines a cavity to hold a motor 800 or other actuator coupled to the moving mirror 212 in the interferometer. This cavity is large enough to allow the motor 800 to translate the moving mirror 212 using blade flexures 810 or other suitable flexures through a relatively long stroke (e.g., >3 mm) to provide a wide range of possible optical path length differences between the interferometer arms. Cavities can also be used to trap light to mitigate surface reflections.

In addition, the optomechanical mounting system 300 includes built-in tip/tilt flexures 310 to securely fasten the spectrometer's mirrors, beamsplitters, lenses, and other optical components to the optomechanical mounting system 300. Each tip/tilt flexure 310 can be adjusted independently and may provide up to six degrees of freedom (e.g., translation along and rotation adjustments about the x, y, and z axes). Together, these tip/tilt flexures 310 provide passive alignment (or factory alignment) for the spectrometer's optical components using the flexure adjustment screws 312. The flexure system may use at least two screws for each axis, with one screw threaded through the flexure and the other screw threaded through the base. When the first screw is tightened the flexure moves away from the base. When the second screw is tightened, the flexure moves towards the base. If both screws are tightened, the overall structure stiffens, thereby helping to reject external disturbances while holding the desired offset position. It is possible to adjust tip and tilt along one bend flexure by placing the two screws parallel to the bend flexure.

FIGS. 4A and 4B show assembled and exploded views, respectively, of a Fourier-transform imaging spectrometer 400 that includes the interferometer 200 of FIG. 2A mounted with the optomechanical mounting system 300 of FIGS. 3A-3D. The exploded view shows that optomechanical mounting system 300 includes several layers of EDM aluminum, including a top cover 402, a top spacer layer 404, an optics layer 406 (to hold the optical components), a middle spacer layer 408, an attachment layer 410, a bottom spacer layer 412, and a bottom cover 414. The layers' surfaces may be anodized to reduce surface reflections and prevent electrical shorts. The number of layers and the layer thicknesses can be scaled up or down, depending on the application and desired dimensions. These layers can be aligned with pins and secured with screws 420 and/or other fasteners.

The assembled spectrometer 400 may be relatively compact, e.g., 17 mm×20 mm×38 mm, and can be fastened to a circuit board 500 that holds the camera 220, the VCSEL 242, the position-sensing photodetectors 248, and other electronics, including not limited to a processor (such as a microprocessor, field programmable gate array (FPGA), or digital signal processor DSP), a memory, and one or more input/output interface as shown in FIGS. 5A-5C. Suitable input/output interfaces include but are not limited to universal serial buses (USBs), RS232 interfaces, Ethernet interfaces, VGA, HDMI, Firewire, LVDS, and WiFi interfaces. The input/output interface can be connected to a computing device, such as a smartphone, tablet, laptop, or onboard screen which displays a user interface 520, shown in FIG. 5D, for controlling the spectrometer 400 and/or processing hyperspectral imagery acquired with the spectrometer 400.

Exemplary spectrometers can also be mounted inside other packages, such as an endoscope, smart phone, scanner gun, microscope, or telescope. Endoscopic spectrometers can be used for a variety of diagnostic applications, including identifying flat, small cancerous lesions and ulcerated tissue in the gastrointestinal tract and other body lumens. They can also be used for image-guided therapy; for instance, the spectrometer may provide hyperspectral imagery that can be used to guide a therapy beam and to gauge the therapy beam's effectiveness at ablating a particular region of tissue, e.g., by determining cancer margins during surgery. An endoscopic spectrometer can also be used to inspect crawl spaces, packages, pipes, holes, etc.

FIGS. 6A and 6B show views of an endoscopic Fourier-transform imaging spectrometer 600 fully assembled on a rotating endoscope tip and in an exploded view, respectively. The endoscopic spectrometer 600 may include a cylindrical housing 602 that contains an optomechanical mounting system 630, which in turn holds a Michelson interferometer 200 as shown in FIG. 2A and a motor 800 or other actuator for varying the optical path length difference between the arms in the Michelson interferometer 200. A photodiode board 610, camera board 612, and motor board 614 hold detector elements (e.g., camera 220 and photodetectors 248), light sources (e.g., VCSELs 242), processor(s), memory, and other electronic components. The components inside the housing 602 can be connected to a flexible conduit 604 that contains electrical, mechanical, and fluid connectors for directing the distal end through a lumen or passage.

2.0 Mirror Actuation

As discussed above, the spectrometer includes one or more actuators for moving the mirrors in the interferometer with respect to each other in order to correct for misalignment and vary the optical path length difference between the arms in the interferometer. The actuator speed depends in part on the desired hyperspectral image acquisition rate: it should be fast enough to move the moving mirror 212 (FIGS. 2A and 2B) such that the spectrometer samples the spectrum at the desired rate. In other words, the actuator bandwidth should be greater than the maximum spectral sampling rate (detector frame rate), which in turn should be greater than the hyperspectral image frame rate. For example, if the desired frame rate (spectral sampling rate) is 2000 fps, then the actuator bandwidth should be about 4 kHz to about 20 kHz or more. If the desired frame rate is 30 fps, then the actuator bandwidth should be about 60 Hz to 300 Hz or more.

Generally speaking, however, it is challenging to provide high-speed actuation and long stroke (translation distance) in a compact package. Piezo-electric devices provide fast actuation, but tend to move over small relative distances (e.g., less than 1% of their length) and hence short absolute distances for small package sizes. In contrast, voice coils and other Lorenz force motors can produce relatively long strokes, even for compact device size, but tend to be relatively slow if high strokes and low power requirements are desired.

Rather than use a single actuation technique, an exemplary spectrometer may include a hybrid actuator that provides high-speed actuation and long strokes in a compact package. This hybrid actuator may include a piezo-electric actuator that is fast enough to provide high-speed control over ranges of picometers to micrometers and a voice coil actuator that provides stroke lengths of micrometers to millimeters. Together, the piezo-electric and voice-coil actuation offer high-resolution positioning (e.g., to a tolerance of within 30 nm) and high stroke (e.g., over distances over 3 mm) for obtaining high-resolution spectra (e.g., with a resolution as fine as 1.6 cm$^{-1}$). This actuation can be combined with feed-forward and feedback control to cancel misalignment due to external vibrations, temperature changes, and other environmental perturbations.

FIGS. 7A-7C show different views of a piezo-electric tip/tilt/translation assembly 700 suitable for the positioning the moving mirror 212 with respect to the static mirror 210 at high-speed in the interferometers 200 and 201 shown in FIGS. 2A and 2B, respectively. To improve the actuation bandwidth, the high-speed actuator may be located on a different mirror than the high stroke actuator as to reduce the overall mass on the high-speed actuator and therefore increase the resonance frequency and bandwidth of the high-speed actuator. The assembly 700 includes piezo-electric stacks 710a, 710b, and 710c (collectively, piezo-electric stacks 710), which are oriented along orthogonal axes to tip, tilt, and translate either the static mirror 210, the moving mirror 212, or another optical component in the interferometer 200, 201. Each piezo-electric stack 710 is fastened in place by a respective pair of screws (denoted 712a, 712b, 712c, 714a, 714b, and 714c in FIGS. 7A-7C; collectively). These screws 712 and 714 can be tightened and loosened for static alignment. Applying a voltage to a particular piezo-electric stack 710 causes the piezo-electric stack 710 to stretch longitudinally (i.e., in the direction of the double-headed arrows), causing the desired tip, tilt, or translation.

For example, actuating piezo-electric stack 710c causes a thinned portion 720 of a flexure to bend about a pivot point 722, which in turn moves the mirror 210, 212 affixed to the assembly 700. Alternatively, the screws 714c and 712b can be replaced with springs or flexures to provide a restoring force to the piezo actuator.

FIGS. 8A-8D show views of a voice-coil actuator 800 for translating the moving mirror 212, which may be attached to a mirror attachment 892, so as to vary the optical path length difference between the arms in the spectrometer's interferometer (e.g., interferometers 200 and 201 in FIGS. 2A and 2B, respectively). In FIG. 8A, the actuator 800 is in its neutral position; in FIG. 8B, the actuator 800 is actuated to shift the mirror (not shown), which can be coupled to the bottom flexure fixture 828. This actuator 800 provides an exceptionally long and linear stroke (e.g., a maximum displacement of about 3 mm), high speed and bandwidth, and virtually unlimited positioning resolution.

The voice-coil actuator includes a wire coil 826, which may have a resistance of 5-15Ω (e.g., 7Ω) wrapped around a bobbin 820 between a pairs of opposing magnets 822a and 822b, 822c and 822d, and 822e and 822f (collectively, magnets 822). The magnets 822 are oriented with their northern poles facing each other to direct the magnetic field through a steel core 832 (FIG. 8C; hidden behind the bobbin 820 in FIGS. 8A and 8B) and around a steel yoke (824). Running a current through the coil 826 causes the bobbin 820 to move with respect to the magnets 822, which in turn bends double compound flexures 810a and 810b (collectively, flexures 810) coupled to the bobbin 820, a bottom flexure fixture 828, a top flexure fixture 840, and the base 830, respectively. These flexures 810 may be 100 μm steel blades an on-axis stiffness of $K_{\theta Fx} \approx 486$ N/m, a torsional stiffness $K_{\theta My} \approx 4.7$ Nm/rad, and a maximum stroke $q_{max} = 3.96$ mm in each direction for a spectral resolution finer than 1.6 cm$^{-1}$. Together, the flexures 810 provide an actuator positioning constant of 370 μm/V. If desired, a second pair of flexures 810 can be reproduced on the other side of the bobbin as shown in FIG. 8D. FIG. 8D also shows these flexures 810 may be offset into the page to increase the torsional stiffness and reduced unwanted top and tilt. The flexures 810 can also be mirrored around the bottom flexure fixture 828 to provide symmetry to further reduce unwanted tip and tilt.

As discussed in greater detail below, the actuator can be controlled using a feed forward and feedback controller. This controller can be used to accurately and precisely position the mirrors with respect to each other and to increase the speed of response of the actuator. The actuator and flexures can also be used to adjust the tip and tilt of the mirrors with respect to each other in order to improve alignment and implement some of the special algorithms described later. For example, the piezo actuators like those in FIGS. 7A-7C may be used to tip and tilt the mirrors. Running current through additional coil wrapped in different directions around the linear actuator bobbin in FIGS. 8A and 8B can also produce small tip/tilt forces.

3.0 Relative Position Sensing

Figures 9A, 9B, 9C:
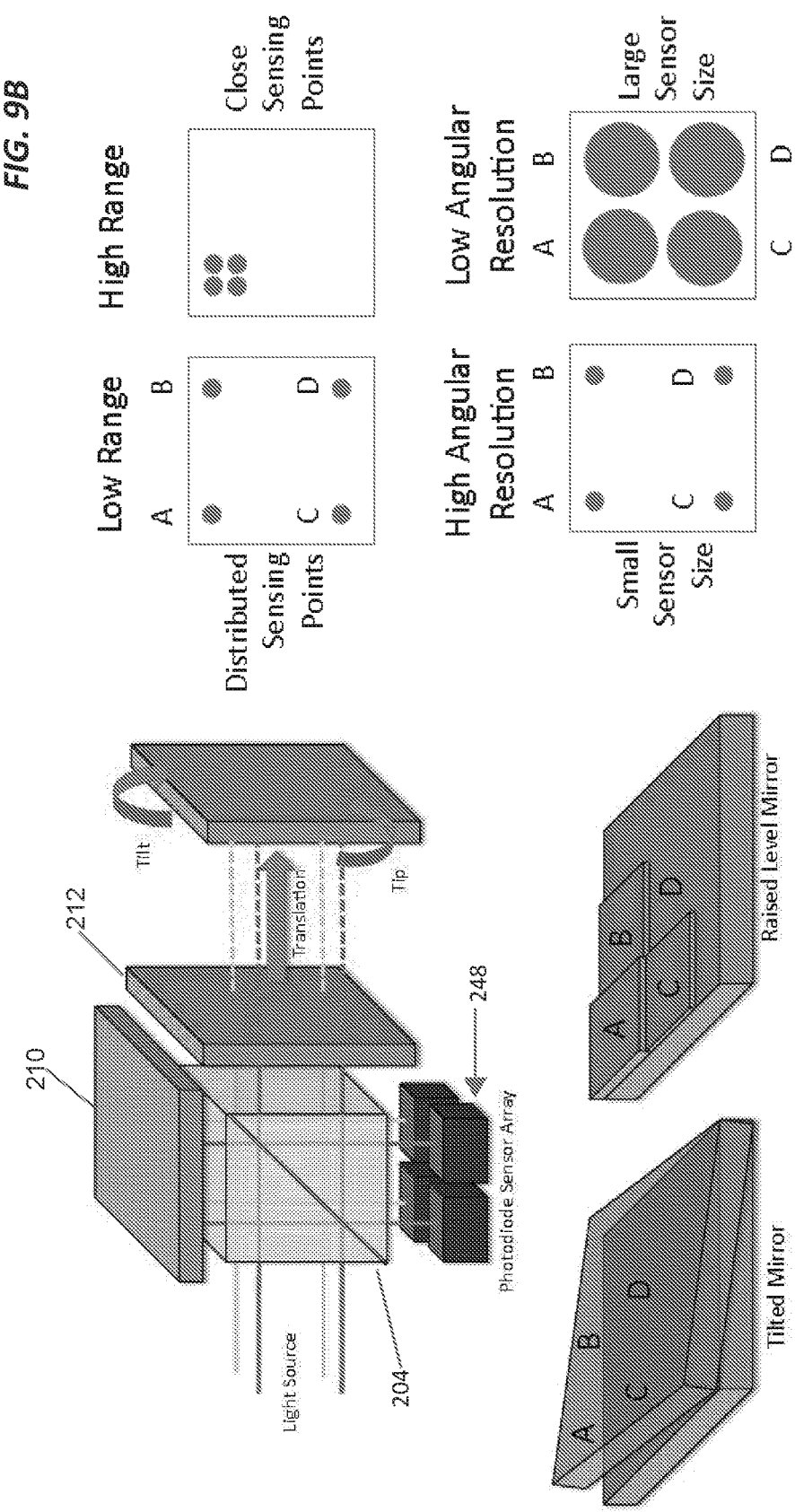
FIG. 9A shows a photodetector sensor array configured to sense the position, tip, and tilt of one mirror in a Michelson interferometer with respect to the position of another mirror in the Michelson interferometer.
FIGS. 9B and 9C illustrate different sensor positions and sizes in the photodetector sensor array of FIG. 9A.

Referring again to FIGS. 2A and 2B, an exemplary Fourier-transform imaging spectrometer may include a miniature, integrated position sensing system 240, 280 that senses the relative positions of the interferometer mirrors with respect to each other. (FIG. 9A shows a simplified representation of the position sensing systems 240, 280 in FIGS. 2A and 2B.) The positioning sensing system may include a miniature 850 nm VCSEL laser that emits a beam with a high coherence length and a bandwidth less than about 0.2 nm. This beam passes through the interferometer and is reflected back towards an analog quadrature encoder. This concept is modified from electronic analog quadrature encoder systems operating under non-interferometric principles. Those of ordinary skill in the art will readily appreciate that the position sensing system may also use other ways of measuring relative mirror position, including phase delay mechanisms, polarization mechanisms, and lasers that emit light at different wavelengths.

To ensure proper positioning, the position sensing system 240, 280 may measure the relative mirror positions at a rate that is greater than the spectral sampling rate (frame acquisition rate). For Nyquist sampling, the position sampling rate may be two or more times the maximum actuator bandwidth. In some examples, the position sampling rate may be about 20 kHz to about 2 MHz (e.g., about 20-100 kHz).

Depending on the embodiment, the positioning sensing system may sense a single laser point for higher angular range (system 240 in FIG. 2A) or multiple distributed laser points (system 280 in FIG. 2B) for lower angular range as illustrated in FIGS. 9B and 9C. The measurement system requires a phase shift between the interferometric signals. The phase shift can be accomplished by tilting the mirror or using a raised level mirror, e.g., as shown in FIG. 9A. If the mirror is tilted slightly by angle θ, the signal on the photodiodes can be calculated as:

$$a(x) = \cos\left(\frac{2\pi x}{\lambda}\right) \quad b(x) = \sin\left(\frac{2\pi x}{\lambda} - \phi\right) \quad \phi = -\frac{\pi}{2} + \frac{2\pi d \sin(\theta)}{\lambda},$$

where x is the optical path length difference between the mirrors, λ is the wavelength, and φ is the phase difference between the two photodiodes due to the mirror tilt. The position of the mirror can be back calculated if the tilt is known and conversely, the mirror tilt can be calculated if the position is known using:

$$x = \frac{\lambda}{2\pi} \tan^{-1}\left(\frac{b(x) + a(x)\sin(\phi)}{a(x)\cos(\phi)}\right).$$

For larger angles, a single laser point measurement can be used (system 240 in FIG. 2A). For smaller angles, a multiple laser point measurement may provide more precise information and has one less optical component for the sampling light to pass through (system 280 in FIG. 2B). The input laser light can be split into more points to measure relative mirror tilt in the axis into the page. Generally speaking, the system should make at least n+1 measurements to resolve n degrees of position. For example, to measure differences in tip, tilt, and translation, the position sensing system should measure four different laser points.

Figure 9E:
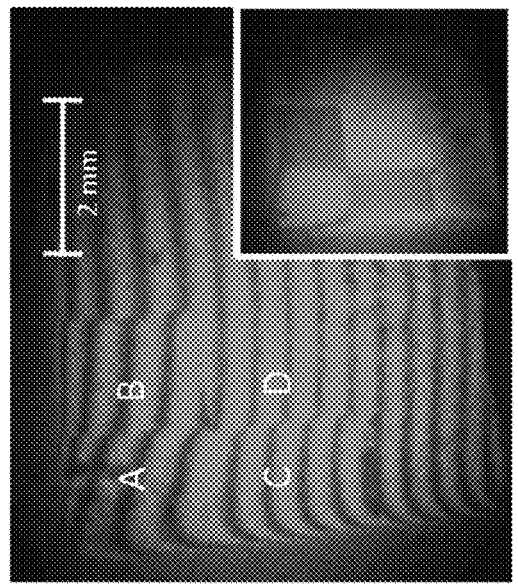
FIGS. 9D and 9E show a scanning electron micrograph (SEM) and an interference pattern, respectively, from a stepped mirror like the one shown in FIG. 9A.
Figure 9D:
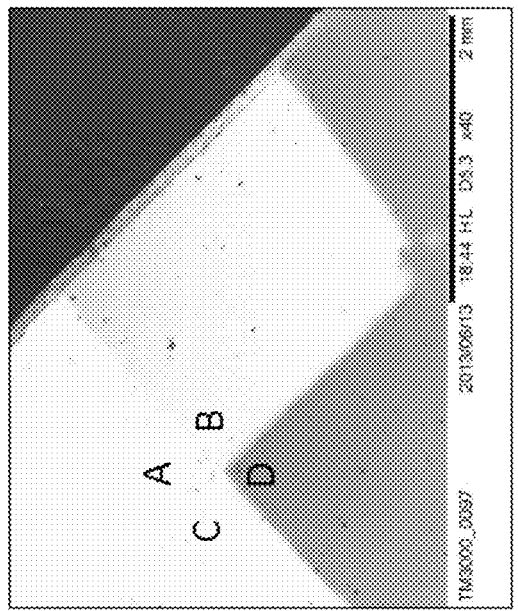

FIGS. 9D and 9E show a scanning electron microscope image and an interferometric image, respectively, of the raised-level mirror shown in FIG. 9A. The raised level mirror allows the mirror to be flat for the imaging spectrometer while still providing a phase shifted signal for the position sensor. The height difference in the raised levels should be on the order of the wavelength of the sensor laser light. For example, for a 850 nm laser, the height difference might be a quarter of a wavelength or 212.5 nm. This can be accomplished using masking and sputter coating or other mirror fabrication technologies.

FIGS. 10A-10D are plots derived from position sensing system measurements of relative mirror position in a Fourier-transform imaging spectrometer. FIG. 10A shows quadrature photodiode signals versus time from a pair of photodiodes that measure the optical path length difference between the interferometer mirrors. FIG. 10B is a Lissajous plot of the normalized photodiode signals from FIG. 10A; it is elliptical and tilted about the origin, indicating a phase difference between the photodiode signals. Since the trace does not go over itself, this shows that the phase changes over time due to tip or tilt. FIG. 10C is a plot of the mirrors' optical path length difference (calculated position) versus time based on the photodiode signals of FIG. 10A. It shows an underdamped oscillation representing motion of the moving mirror from a neutral (zero-offset) position by a distance of about 10 µm. FIG. 10D shows the photodiode signal phase difference (noisy trace) and calculated mirror velocity (smooth trace) versus time for the mirror. In this experiment, the velocity and phase shift match due to the fact that the mirror is cantilevered on a thin attachment beam that bends and oscillates as the mirror moves. The cantilever effect can be used to measure the mirror velocity by calculating the phase change over time. The velocity to phase coupling can be removed by making the cantilever thicker.

4.0 Spectral Results

Figure 11B:
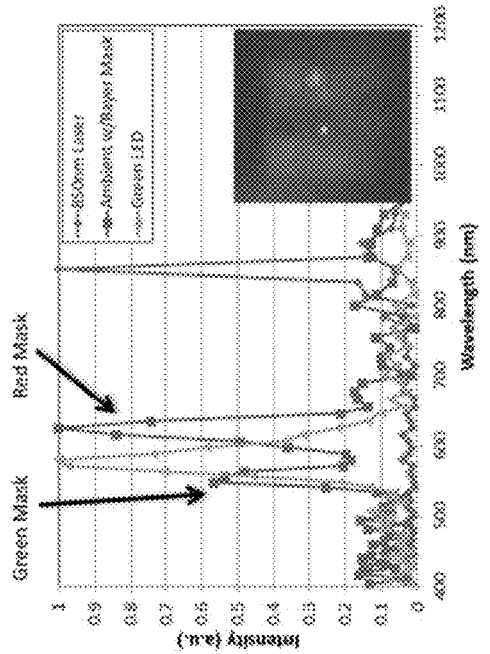
FIGS. 11B, 11C, and 11D show the spectra of the data shown in FIG. 11A, white light, and propidium iodide fluorescence, respectively.
Figure 11D:
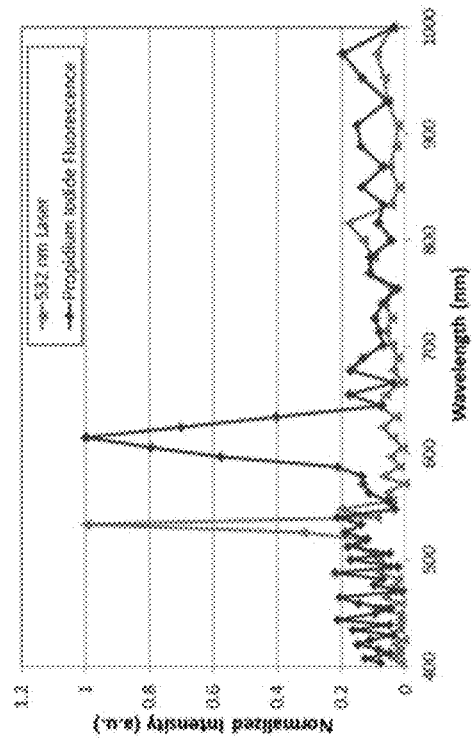
Figure 11A:
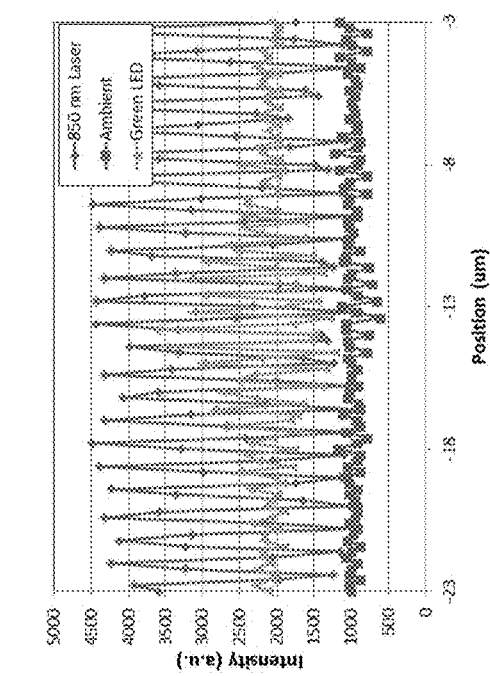
FIG. 11A is a plot representing detected intensity versus relative mirror position and spectra for an exemplary spectrometer illuminated with infrared light (upper trace), green light (middle trace), and ambient light (lower trace).

Several different types of spectral results can be obtained from this imaging spectrometer. The spectrometer takes a single image at each spectral position and each of the pixels on this image can produce spectra when a series of images are taken. FIG. 11A shows the intensity of three different pixels in a series of 100×100 pixel images as the position is changed. One of these images is shown in the inset of FIG. 11B. The three pixels chosen are from an incoherent green LED (green dot), a 850 nm laser (purple dot), and the ambient light (white background). The resulting spectra from the Fourier transform of the information in FIG. 11A is shown in FIG. 11B. The expected broad peak from the green LED at 570 nm is shown along with the sharp peak for the 850 nm laser. The white ambient light shows the red and green color filter lines of a Bayer mask.

Figure 11C:
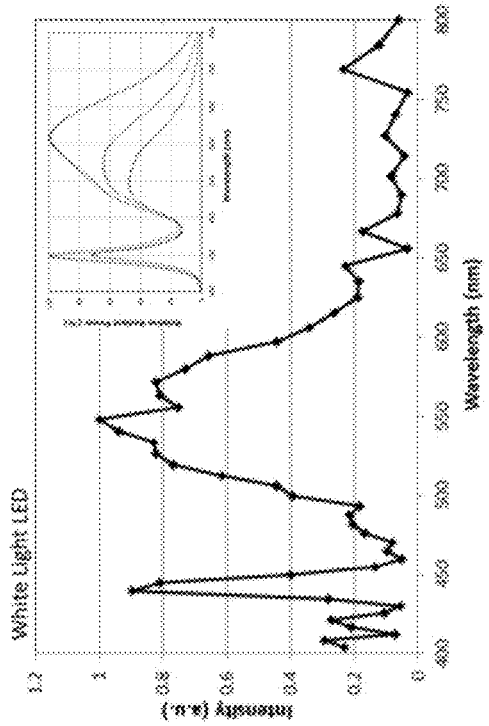

The types of spectra that can be obtained with the imaging spectrometer can include light sources with low coherence such as white LEDs as shown in FIG. 11C. Reference white LED spectra are shown in the inset and match well with the measured spectra. In addition to measuring pure light sources, fluorescence samples can also be measured. FIG. 11D shows the input light at 532 nm and the light emitted by the fluorescence of a sampled dyed with propidium iodide with a peak at 615 nm. Similar to the analysis of fluorescence spectra, the device can be used to measure Raman spectra of a full image for applications such as analyzing unknown compounds or analyzing the chemical composition of diamonds. The device can also be used to measure the blood oxygen content of different parts of an animal by comparing the oxygenation levels of the blood at two different wavelengths (e.g., 650 nm and 980 nm).

Figure 12B:
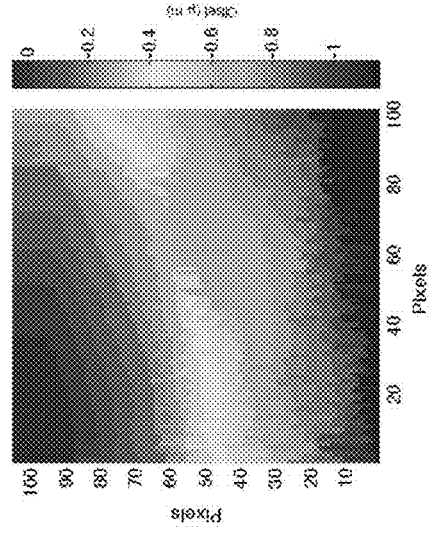
FIGS. 12A and 12B show a plot of intensity versus optical path length difference and a hyperspectral image, respectively, of a white light.
Figure 12A:
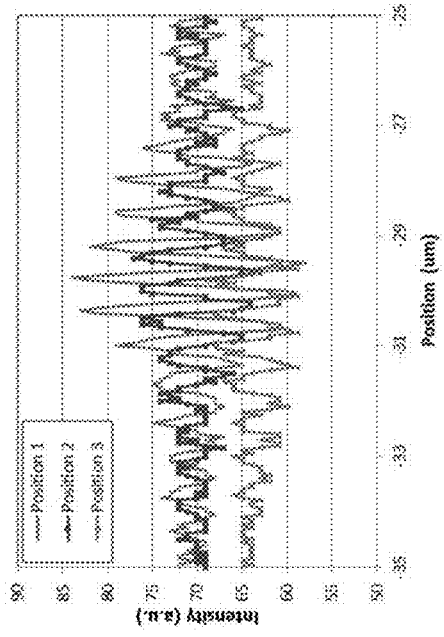

In addition to analysis that can be completed on a single pixel, analysis can also be done on a full image. In FIGS. 12A and 12B, a white light source is placed over the entire imaging area and the resulting spectra are measured. This shows the use of the device as a white light interferometer (an interferometer which measures small offsets, rather than spectra, of reflective objects). The data from three pixels at different positions is shown in FIG. 12A. In this figure, the spectra do not line up perfectly in terms of the position axis because the mirrors are slightly tilted with respect to one another. By cross correlating the spectra of different pixels in the image, it is possible to show how far the offset of each pixel is with respect to the others. For the full image, the overall offset from corner to corner of FIG. 12B is about 1 µm.

Figure 13B:
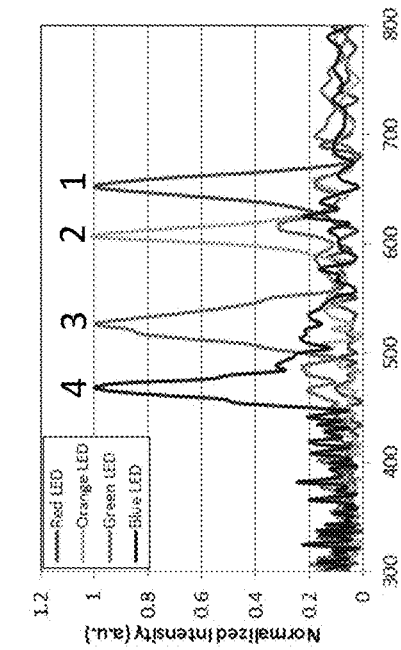
FIGS. 13A and 13B show images of an LED test array as well as the reconstructed color image from the spectral data and the spectra of part of the LED test array, respectively, acquired using an exemplary imaging spectrometer.
Figure 13A:
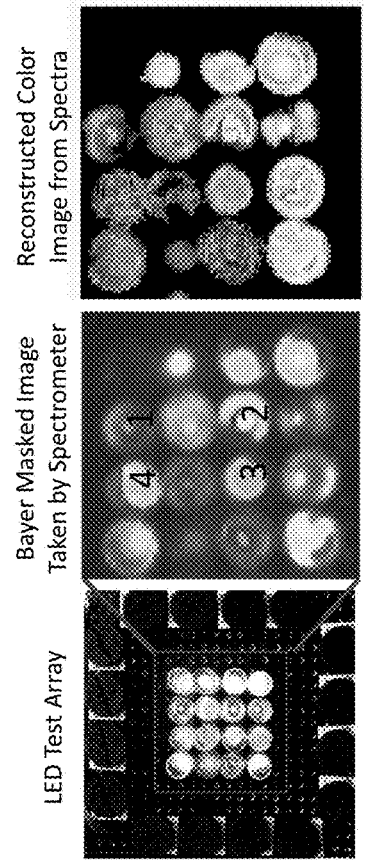

FIG. 13A shows another application of the imaging spectrometer where an array of color LEDs are measured using the spectrometer. A series of Bayer masked images taken by the spectrometer can be converted to black and white intensities and Fourier transforms taken of each pixel. In positions 1 through 4, which show red, orange, green and blue LEDs, respectively, the spectra can be obtained and are shown in FIG. 13B. The Fourier transform information preserves the color information and can be reconstructed as a color image by mapping the spectra of each pixel into red, green and blue color bins (shown here in grayscale). These color bins can be remapped into a RGB (red, green blue) image and the intensity levels can be manipulated to create the reconstructed color image shown on the right of FIG. 13A. The color in this figure matches well with the original Bayer masked image obtained from the spectrometer.

5.0 Mirror Position Control

As mentioned above, mirror positioning affects the data acquired in imaging spectroscopy. Unlike continuous sensor spectroscopy, where the signal of the interferogram can be read out continuously, imaging spectroscopy involves acquiring an entire image at once. Any motion of the mirrors during the image intensity integration time may result in a smeared interferogram. For imaging spectroscopy, maintaining the sampling position for the entire integration time for each image reduces the likelihood of image distortion. However, the speed with which the mirror moves from one position the next position between image integration times affects the data acquisition rate. For high-speed, stable operation, the mirror(s) should change position quickly and remain stable during image integration.

Figure 14:
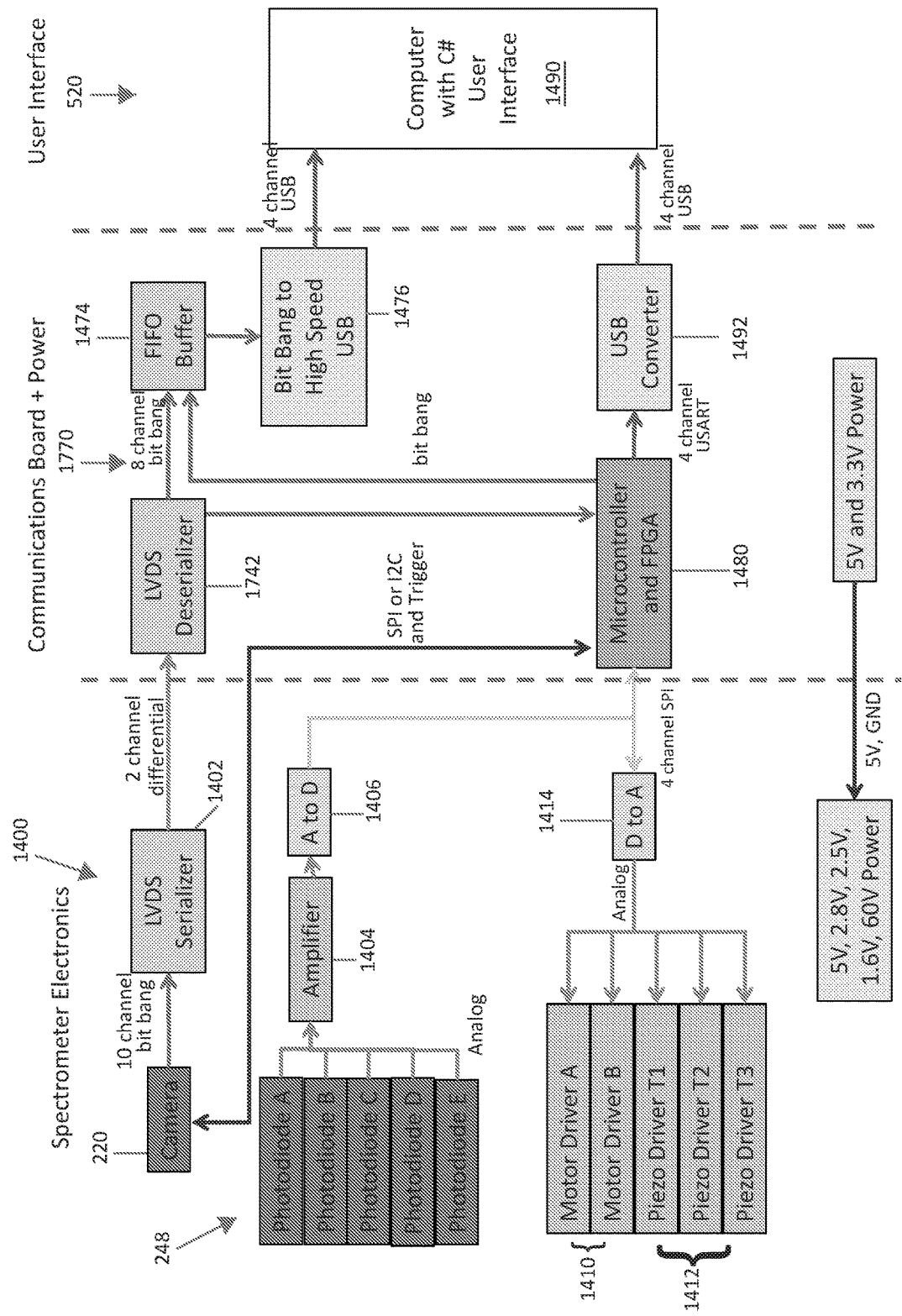
FIG. 14 is a block diagram illustrating electronics for controlling a compact hyperspectral imaging spectrometer.

FIG. 14 shows a block diagram of the spectrometer electronics 1400, communications and power hardware 1470, and the user interface 520 of an exemplary imaging spectrometer. The spectrometer electronics 1400 include the camera 220 and a low-voltage differential signaling (LVDS) data serializer 1402, which is coupled to an LVDS deserializer 1472 for transferring information. This information is buffered in a first-in, first-out (FIFO) buffer 1474 and then sent through a high speed USB bus 1476 to a computer 1490 which houses the user interface 520. This information can also be stored or sent directly to a screen.

The data can also be sent for analysis to one or more processors, such as a microcontroller and a field-programmable gate array (FPGA) 1480. The microcontroller and FPGA 1480 interface with the computer 1490 using another USB interface block 1492 and communicate with the camera 220, position-sensing photodiodes 248, and motor/piezo controllers through serial peripheral interface (SPI) or inter-integrated circuit (I2C) interface (not shown). The position-sensing photodiodes 248 are coupled to the microcontroller/FGPA 1480 via a transimpedance amplifier 1404 and an analog-to-digital converter 1406. Note that photodetectors A through D are used for high-speed position control while photodetector E is used as a white light center reference.

The microcontroller/FGPA 1480 is also coupled to motor drivers 1410 and piezo drivers 1412 via a digital-to-analog converter 1414 to provide power to the actuators (e.g., piezo-electric tip/tilt/translation assembly 700 and motor 800). For each camera frame, the camera 220 or the microcontroller 1480 generates a trigger signal. This trigger signal tells the microcontroller 1480 to move the moving mirror 212 (FIG. 2A) to the next desired position quickly in a controllable fashion. This causes the microcontroller 1480 to compute the necessary signals to send to the motor drivers 1410 and the piezo drivers 1412. The microcontroller 1480 monitors the photodiode signals to determine if the input signals need to be modified. Once the position is achieved, the microcontroller 1480 attempts to hold the desired position (rejecting external vibrations using the actuators) for the full integration period on the camera 220 before receiving or obtaining a new trigger signal for the next frame.

5.1 Types of Control Modes

Figure 15A:
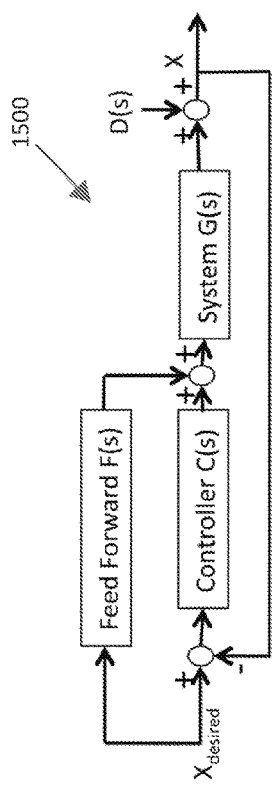
FIG. 15A is a block diagram that illustrates feed-forward and feedback control of an actuator that moves one or more optical elements in an interferometer.

In order to hold a position and reject disturbances, feedback and feed forward controllers are designed for each actuator in the system. A simplified representative controller architecture 1500 for the motor actuator 800 is shown in FIG. 15A. (Similar control architectures can be used to control the piezo actuators 700.) In one example of this architecture 1500, the system G(s) represents the motor actuator 800 and the controller C(s) and feed forward F(s) can be implemented with the microcontroller/FPGA 1480 shown in FIG. 14.

Figure 15B:
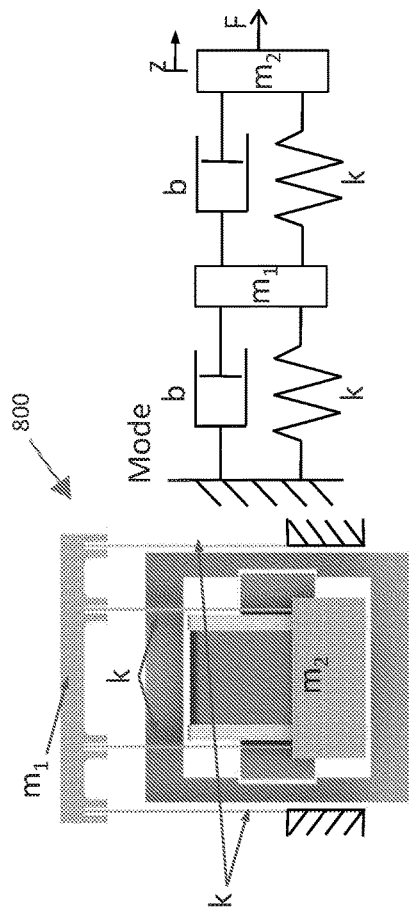
FIG. 15B illustrates the transfer function of the voice coil actuator shown in FIGS. 8A and 8B.

FIG. 15B shows the system transfer function of the motor 800 showing the spring constant of the flexures k, the damping from eddy currents and other losses b, and the mass of the different components m. The system transfer function G(s) models the four poles and two zeros that dominate the system. This transfer function can then be used to design the optimal feed forward and feedback controllers shown in FIG. 15A using proportional-integral-derivative (PID) control, loop shaping, full state feedback, full state inversion feed forward, adaptive feedback or other control techniques. FIG. 15A shows the system control response transfer function along with the external disturbance rejection transfer function.

5.2 Feedback and Feed Forward Control

Feedback control can be achieved by measuring the position signal from the position-sensing photodetectors 248 and then modulating the input signal (voltage) to the motor 800 as a function of the measured position. Feed forward control is done by understanding the dynamics of the system and predicting the input necessary to achieving the desired output. Because motors and piezos have inherent dynamics, simply sending the desired position to the motor drivers may not be sufficient to obtain the desired position quickly with low oscillation (oscillation of the mirror position causes smearing of the intensity measurement). Thus, the microcontroller/FPGA 1480 may implement open-loop or closed-loop control of both the motor and the piezo(s).

Figure 16A:
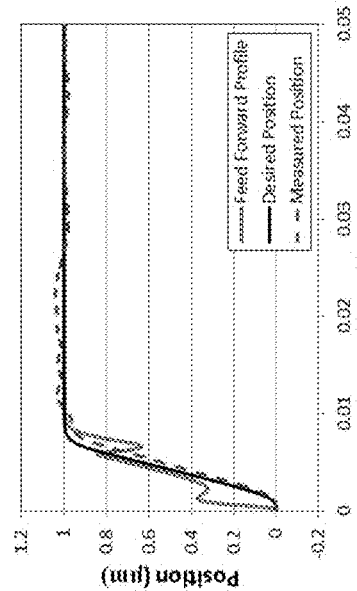
FIGS. 16A-16D show plots of mirror position under open loop and closed loop control with and without full model inversion feed forward components.
Figure 16C:
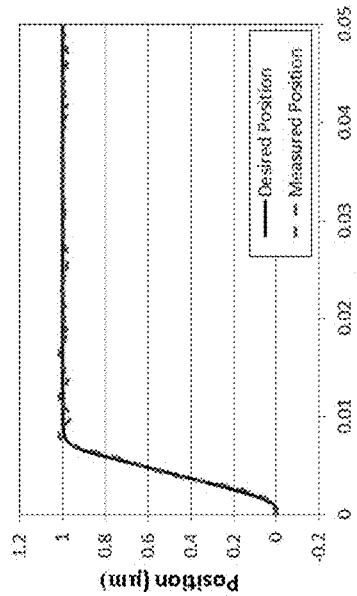
Figure 16B:
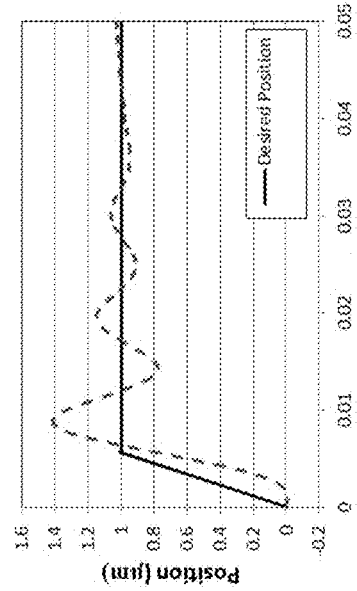

FIGS. 16A-16D show the open-loop (FIGS. 16A and 16C) and closed-loop (FIGS. 16B and 16D) step response for simple feed forward control (e.g., slew rate ramp and low pass filtering) and full-model inversion feed forward control. FIG. 16A shows that with the simple feed forward input of a simple ramp in open loop (no closed loop feedback control), the measured position of the actuator oscillates before being slowly damped away over a period of about 80 ms. This relatively long settling time could result in acquisition of smeared spectral information over the camera integration period. FIG. 16B shows that applying closed loop feedback in the form of a proportional, integral, derivative controller (PID), and applying a low pass filter around the feed forward ramp, it is possible to reduce the oscillations dramatically. More specifically, FIG. 16B shows that closed loop response with a feed forward term takes less than 10 ms to settle and holds the desired position well. The settling time limitation is directly related to the slew rate limitation, which can be improved through changing the motor dynamics. Without disturbance rejection terms, the system is limited to about 60 nm resolution and is sometimes as high as 200 nm. With disturbance rejection, we can decrease the external vibrations to about 30 nm and can be further improved using higher resolution digital to analog converters and improved flexure modeling.

In addition to feedback control, more advanced feed forward control can be implemented. As shown in FIG. 15A, including input ramps and low pass filters permits simple feed forward modifications. These simple feed forward modifications reduce the frequencies present in the input and therefore provide less high frequency modulation to the motor, thereby reducing oscillation.

Other forms of feed forward control can be implanted if the full model of the system is known. This information can be obtained by constructing an accurate model of the actuator or by performing system identification methods to the system. System identification methods can include simple step responses, sine sweeps or stochastic system identification methods. Once the system is identified nonparametrically, a parametric model can be fit to the data. This model can then be used to create a full model inversion feed forward controller by inverting the model. There are several ways to invert the model.

A traditional mathematical full inversion is sometimes challenging or even impossible to implement or would be unstable if implemented. In this case, the microcontroller/FPGA 1480 uses a complete mathematical inversion and a higher-order low-pass filter with a cutoff frequency that is much higher than the systems highest resonance of interest. For example, if the system is 4th order (4 poles, 2 zeros), as shown for G(s), this model can be simplified into a single 2nd order system (2 poles). Applying a mathematical inversion makes the system acausal (2 zeros). Then, applying a 4th order filter to the system makes the system causal (total of 2 zeros, 4 poles). This causal inverted model can then be used in the feed forward control module.

There are several possible ways to implement this feed forward model including pre-computing the desired feed forward trajectories from the known desired positions using a convolution of the time domain causal inverted model with the time domain position profile. Another possible method is to generate discrete time domain equation from the causal inverted model and pass the desired position profiles through the discrete equation in real time.

FIG. 16C shows the result of using just the full model inversion feed forward process with no feedback. The desired position includes the ramp and low pass filtering. The causal inverted model is then applied to the desired position with just the ramp (low pass filtering is already built into the causal inverted model) to produce the feed forward profile. FIG. 16C shows that the feed forward profile predicts the effects of the dynamics of the motor system and preemptively provides additional feed forward commands that prevent those oscillations from happening. As a result, without any feedback, the final measured position matches very well with the desired position with almost no oscillations.

Figure 16D:
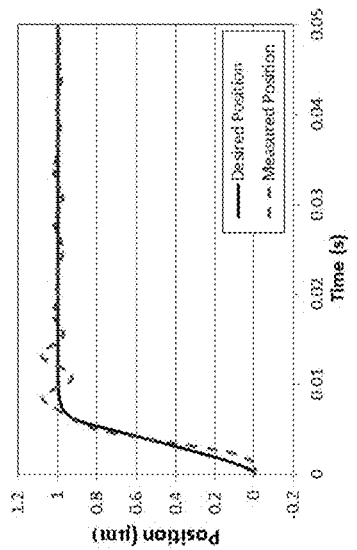

FIG. 16D shows the position versus time when feedback is added to the system.

Here, the full model inversion feed forward method is applied with closed loop feedback and the result is a system that almost perfectly matches the desired position with very little oscillation. In practice, even if full model inversion feed forward provides sufficiently good results, a feedback system reduces the effect of external disturbances (vibrations when the spectrometer is bumped, temperature effects, etc. . . . ) that are not modeled or cannot be sensed independently.

5.3 Adaptive Control

Adaptive control can be thought of as a method of determining the system model at the same time as providing feed forward and feedback control, instead of doing these as two separate steps. It is useful if the system transfer function changes over time due to unmodelled effects like temperature or due to nonlinearities. One such method is to combine stochastic system identification methods with feed forward and feedback control. In this method, a stochastic signal, e.g., in the form of a signal dither (a small random oscillation), is added to the desired position. As the system moves to different desired positions, the input and output data can be used to compute the dynamic transfer function of the system and this information can be used to update the system model in real time. For every input and output data pair, the model is updated slightly and therefore the optimal response is updated. Therefore, if changes happen to the system, the feed forward model can adapt to these changes to provide the optimal feed forward parameters and feedback parameters for control.

The dither may activate all or substantially the frequency modes in the actuator so that there is enough information at all the frequencies to create an accurate model. The dither, however, may also cause the actuator to vibrate slightly, adding to the spectral smearing. Therefore, the dither magnitude should be big enough to provide the desired frequency response information but small enough to prevent undesired spectral smearing.

5.4 Tip-Tilt-Translate Control

Controlling the relative tip, tilt, and translation of the mirrors can improve alignment in real time and reduce the effect of unmodelled disturbances. As discussed above (e.g., with respect to FIGS. 7A-7C, 8A, and 8B), there are several possible ways to implement tip and tilt control including using piezo actuators (stacks, benders, tubes, etc. . . . ) and wrapping additional coil around the linear actuator bobbins in different orientations to produce small tip and tilt forces. When multiple actuators and multiple modes with multiple sensors are included, full state feedback methods and multi-axis control methods can be implemented to achieve control in all the desired states and axes. In state space control, each of the states is fully modeled and a single controller or multiple controllers manage the outputs to control all the states simultaneously. For example, for the voice coil actuator, there are at least two energy storage elements that provide at least two states.

Figure 17:
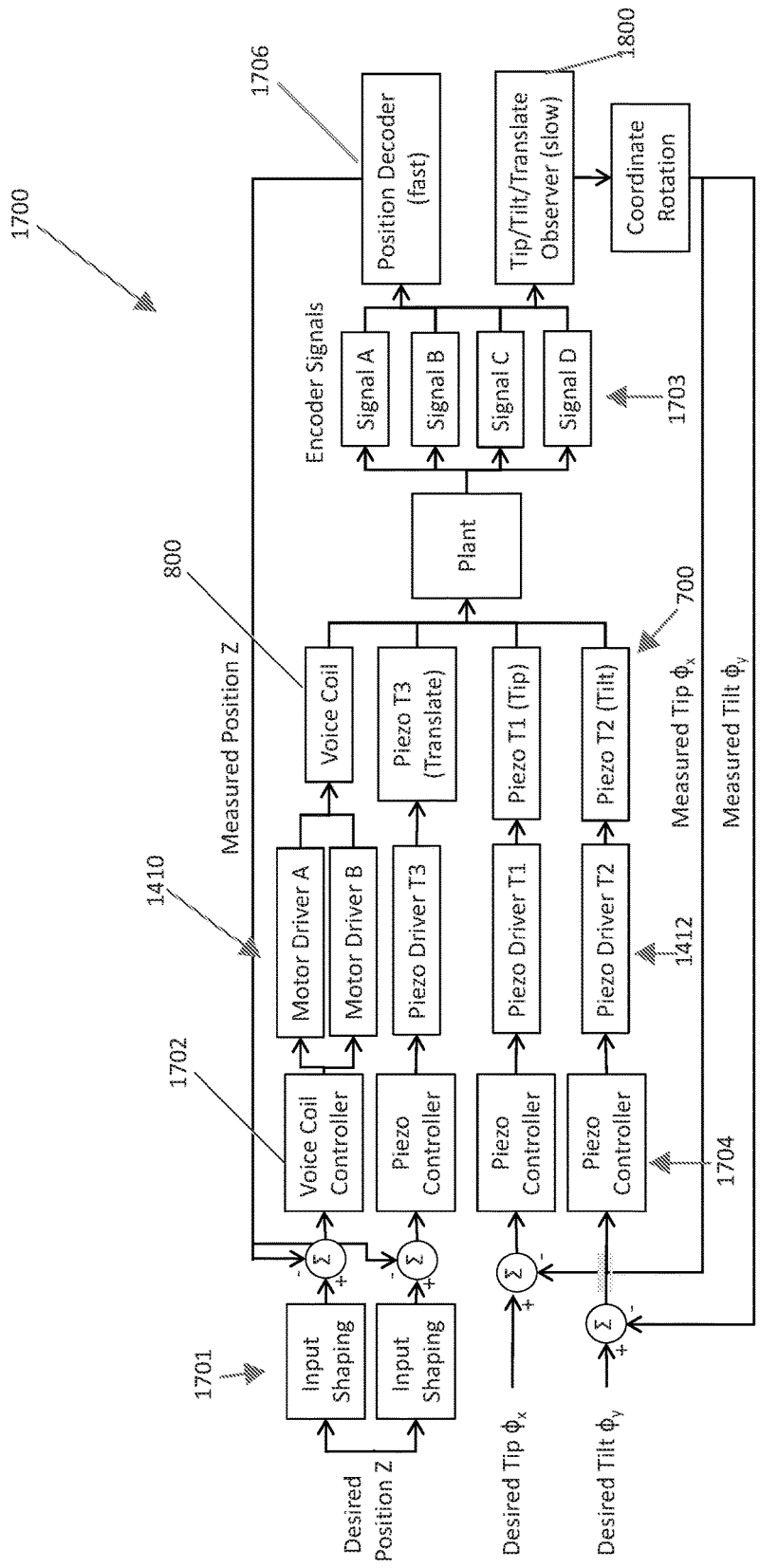
FIG. 17 is a block diagram of a system for closed-loop, multi-axis positioning of one or more optical elements in an interferometer.

For multi-axis control, each axis is managed by a single controller or multiple controllers. FIG. 17 shows a controller architecture 1700 for the actuators involved in multi-axis control, including a voice coil controller 1702, piezo controllers 1704, actuator drivers 1410 and 1412, and the plant itself (moving mirror 212, piezo motor assembly 700, and voice coil motor 800). The user interface 520 (FIGS. 5D and 14) may provide input shaping information 1701 to the voice coil controller 1702 and piezo controllers 1704, which may be implemented the microcontroller/FPGA 1480 or other processor. As described above (e.g., with respect to FIGS. 2A, 2B, and 9A-9E), the plant is observed by the position-sensing photodetectors 248 (not shown), which provide four encoder signals 1703 that can be decoded into position using a fast position decoder algorithm 1706 implemented in the microcontroller/FPGA 1480 or other processor. The encoder signals 1703 can also be used to decode the relative positions into tip, tilt and translation using a complex observer algorithm 1800, which can also be implemented in the microcontroller/FPGA 1480 or other processor. The complex observer algorithm 1800 can be further modified by a coordinate rotation so that the tip axis matches the tip actuator and the tilt axis matches the tilt actuator. (For the tip and tilt axes, separate controllers were implemented to maintain tip and tilt angles. Since tip and tilt angles are largely predictable and desired changes in tip and tilt compensation are small, the control loop for tip and tilt can be run much slower than the controllers for translation.)

Figure 18B:
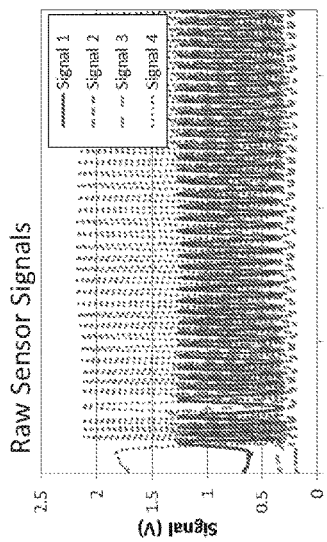
FIGS. 18A-18D illustrate a phase-fit observer process and its ability to decode raw sensor signals (FIG. 18B) into separate signals for translation, tip, and tilt of one or more optical elements in an interferometer.
Figure 18C:
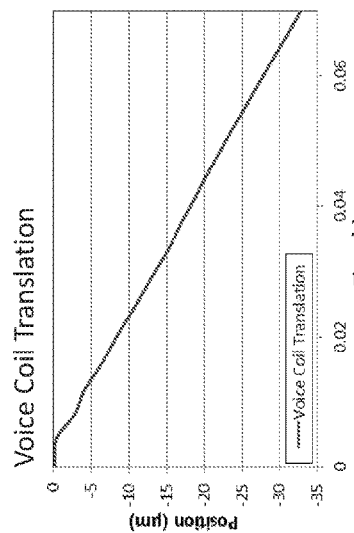
Figure 18D:
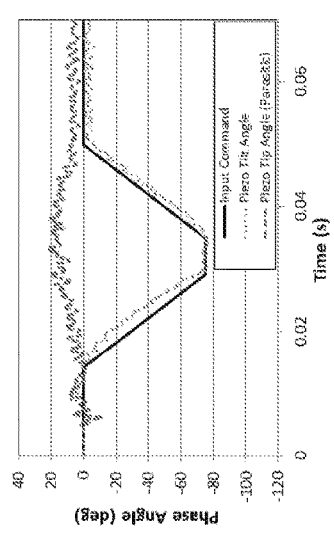
Figure 18A:
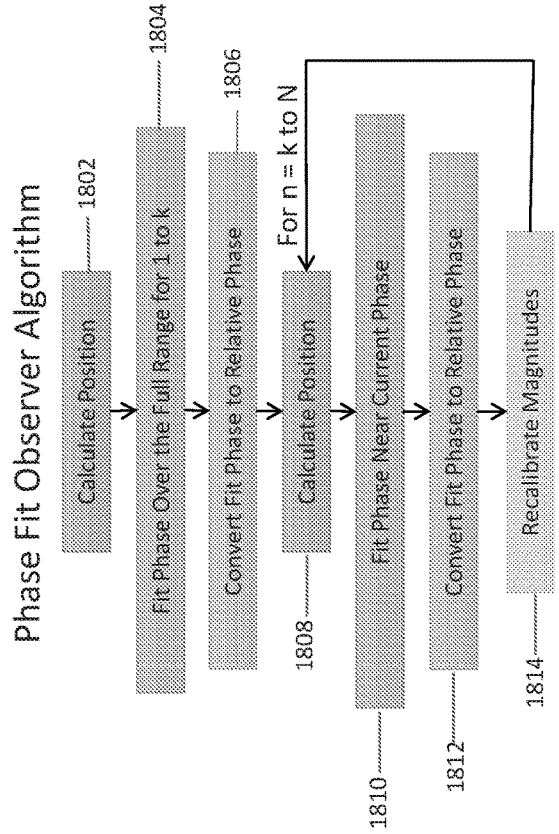

FIG. 18A is a flow chart that illustrates the tip, tilt, translate observer algorithm 1800. In step 1802, the microcontroller 1480 calculates the position from two of the raw sensor signals for samples from n=1 . . . k. In step 1804, the microcontroller 1480 uses a fitting algorithm and the calculated position to fit the phase values as a function of position for all four raw sensor signals. Then these phases are converted to relative phases (relative to one another) in step 1806. This provides the initialization data. Next, in steps 1808, 1810, and 1812, for the samples n=k . . . N, the microcontroller/FPGA 1800 calculates position, fits the phase for the new set of data (the fit is done near the current phase values to prevent phase wrapping), and converts the fit phase to relative phase. Lastly, the microcontroller/FPGA 1480 rescales the magnitudes of each signal to account for signal level changes (step 1814).

The results of this algorithm are shown in FIGS. 18B, 18C, and 18D. The raw sensor signals are first scaled and run through the algorithm and the resulting voice coil translation and piezo tip and tilt are produced. The complex raw sensor signals in FIG. 18A correspond to the combined movement of a voice coil ramp output (FIG. 18B) and a piezo triangle function output in tip angle (FIG. 18C) but little to no change in the tilt angle. This algorithm can therefore be used to decouple the different tip, tilt and translation states so that controllers can be implemented.

5.5 Hybrid Actuator Fast Translation Control

As discussed above, a single low-noise actuator may not be able to provide both high-speed actuation and large mirror displacement(s) at the size, weight, and power of an exemplary spectrometer. Thus, an exemplary spectrometer may include a voice coil actuator 800 (FIGS. 8A and 8B) that provides large displacements, albeit with slower dynamics due to the low stiffness required for longer stroke actuation, and a lower-stroke piezo actuator 700 (FIGS. 7A-7C) with a much higher bandwidth. By combining the two actuators, it is possible to get high speed translation at the same time as large displacements.

Figure 19B:
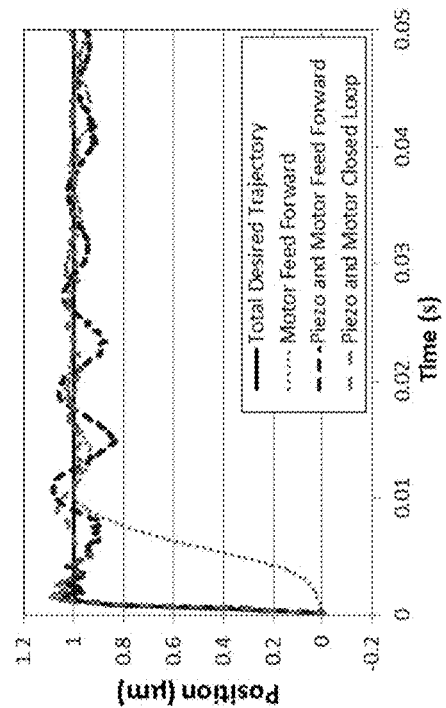
FIGS. 19A-19D are plots that illustrate single-step and multi-step input shaping for high speed hybrid control of piezo and voice coil actuators.
Figure 19D:
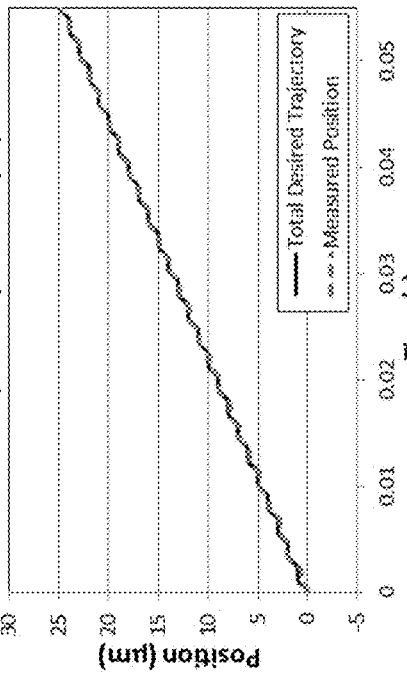
Figure 19A:
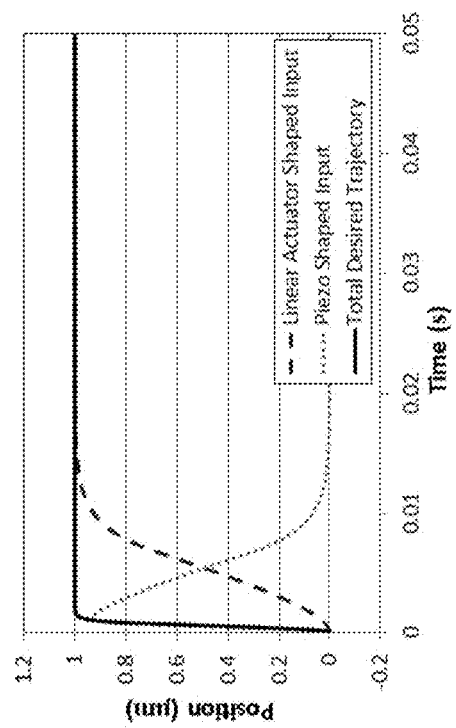

FIG. 19A illustrates a hybrid fast translation control that involves input shaping techniques in order to account for the differences between the voice coil actuator and the piezo actuator. First, the achievable linear actuator trajectory is produced. The final high speed desired trajectory is then generated. These two trajectories are subtracted in order to produce the shaped input for the piezo. Note that the input shaping method takes into account the fact that the linear actuator may not act quickly and that the total piezo translation is limited. Therefore, the piezo position is brought back to zero with each step of the voice coil actuator.

FIG. 19B shows the results of this scheme. With only the motor feed forward component, only a slow motor step is completed. With the piezo actuator feed forward component added, the final position is achieved quickly. When the closed loop controller is added to the motor, much tighter control can be achieved on the position. Since only relative mirror positions are measured and there are two actuators, accurate prediction of the behavior of at least one of these actuators should be known and a controller can be wrapped around either actuator. The high speed controller, in this case, decreases the step time from 10 ms to about 1 ms thereby increasing the translation dramatically allowing for faster imaging frame rates. Stiffer translation piezo assemblies can increase decrease the step time even more.

Figure 19C:
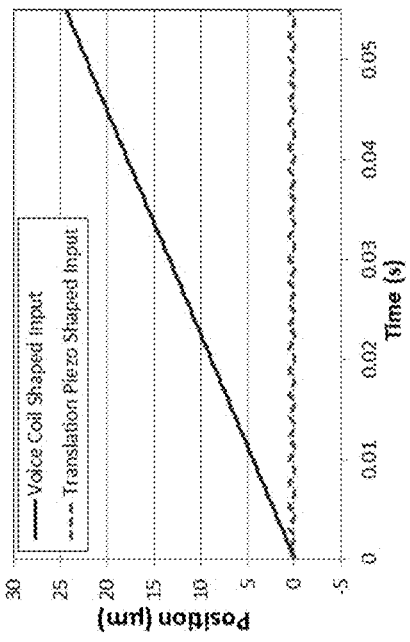

FIG. 19C shows how this can be extended to taking multiple steps very quickly. The shaped input for the voice coil for multiple steps becomes a simple ramp while the translation piezo shaped input becomes a series of small sawtooth triangles. The final total trajectory is shown in FIG. 19D, which is a series of steps to different positions. This also shows that the measured position of the total relative mirror positions matches up well with the desired trajectory.

5.6 Disturbance Rejection

Figure 20:
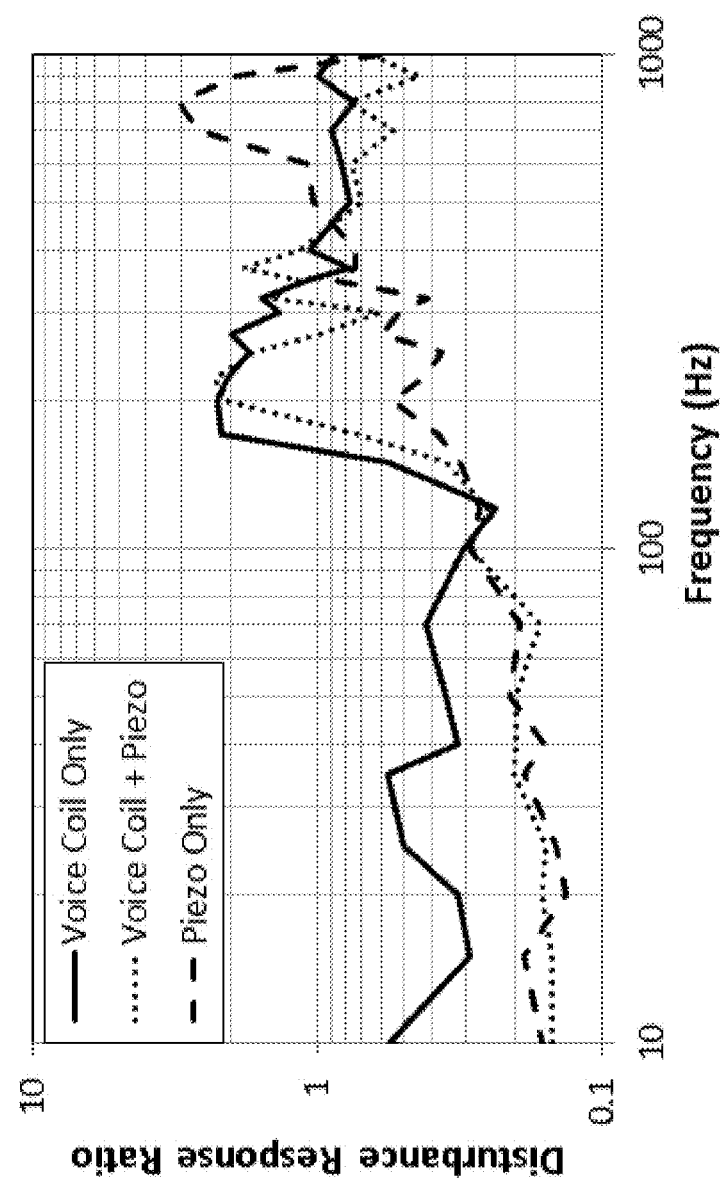
FIG. 20 is a plot of the disturbance response/rejection ratio versus frequency for a mirror whose position is actuated with a voice coil only, a piezo only, and a voice coil together with a piezo.

Another aspect of the present disclosure is the controller's ability to reject external disturbances, whether these disturbances are slow (offsets, misalignments, temperature drift, etc. . . . ) or fast (external vibrations, motions associated with a human holding the device, etc. . . . ). The disturbance rejection of the device for different controller configurations is shown in FIG. 20. The disturbance rejection capabilities of the device are associated with the system dynamics and the design of the feedback controller. If only the voice coil is used, the disturbance rejection tends to be good up to the resonance frequency of the actuator. If a piezo controller is used, the disturbance rejection is even better for low frequencies up to the resonance of the piezo. With hybrid control (e.g., voice coil and piezo with the controller wrapped around the piezo), the low frequency disturbance rejection is comparable to the piezo but rejection is only good up to the voice coil resonance. In practice, mechanical noise tends to be higher at relatively low frequencies meaning the controllers have relatively good rejection in the regions of interest.

6.0 Spectral Sampling

The Fourier transform can be used to convert interference patterns into spectra. This however has many limitations. First, the data are sampled at evenly spaced intervals at or above the Nyquist sampling interval (half the interval of the lowest wavelength present in the system) and a single continuous pass in one direction is conducted over the interferogram—that is, the data are sampled regularly. This means that a large number of samples are needed. For example, achieving a 5 nm resolution at $\lambda_0$=850 nm equates to 700+ samples. If the camera is 30 frames per second, gathering a full hyperspectral image may take up to 23 seconds. Even for a high-speed camera at 2000 frames per second, a video rate spectrum could not be achieved.

In order to reduce the sampling rate while maintaining the desired resolution, an exemplary spectrometer may use one of a variety of irregular sampling methods in order to provide full spectral images quickly and accurately. This provides high resolution spectra at high speed and does not rely on constant sampling at a given velocity like other Fourier transform designs. Examples of these several irregular sampling techniques include but are not limited to under-sampling, non-uniform sampling, optimal sampling, adaptive sampling, and recursive sampling (where the same sample locations are sampled recursively, back and forth).

Figure 21:
FIG. 21 is a table that shows different sampling routines suitable for use with an exemplary imaging spectrometer depending on the amount of prior knowledge of the spectra.

The choice of sampling technique may depend on the amount of previous information known about the spectra being acquired (sample being imaged) as shown in FIG. 21. If there is no prior knowledge of the spectra, a uniform or regular sampling algorithm may be used in conjunction with a fast Fourier transform solution technique or some form of $L_2$ solver. If the band limits are known (e.g., the sensor bandwidth or the fluorescence emission band), then aliased uniform sampling or under-sampling can be used. If the spectrum is known to be sparse, as in the case of Raman spectra or laser light, it is possible to use orthogonal basis sampling or random sampling in conjunction with compressed sensing techniques that utilize $L_1$ solvers. Fast orthogonalization (FOS) can also be used in this case. If the exact spectral locations are known, other methods can be used to optimally sample the spectra.

6.1 Solution Method

The following equation represents a flexible solution for computing the Fourier or Hartley transform in a way that accommodates different irregular sampling algorithm $$y(n) = \sum_{m=1}^{M} A_m P_m(n) + e(n),$$

with matrix form Y=PA+E, where $P_{2i}(n)=\cos(w_i x(n)/c)$ and $P_{2i+1}(n)=\sin(w_i x(n)/c)$. Here y(n) is the interferogram intensity, e(n) is the error, and $A_m$ contains the spectral information. The matrix $P_m(n)$ is constructed from real trigonometric polynomials and contains the guesses for different frequencies $w_i$ and the locations where measurements are taken x. There are many possible ways this can be solved including using an $L_2$ norm solution, which is also known as the least squares algorithm $\hat{A}=(P^T P)^{-1} P^T Y$, and $L_1$ solutions using basis pursuit or linear programming. Note that $L_1$ solutions used in undersampling applications are also sometimes known as compressive sensing algorithms, $$\min_A \|A\|_1 \text{ s.t. } Y = PA.$$

Once the solution A is obtained, the results can be mapped back to a magnitude and phase:

$$M_i = \sqrt{A_{2i}^2 + A_{2i+1}^2}, \phi_i = \tan^{-1}(A_{2i+1}/A_{2i}).$$

The magnitude $M_i$ can be directly plotted against the desired positions $w_i$ to form the familiar spectra. Note that this is a Hartley transform and not a Fourier transform as all constants are real. Also note that there is no restriction on sampling interval thereby allowing non-uniform sampling and under-sampling. The flexible form of the matrix P allows for any choice of desired frequencies thereby enabling adaptive sampling. The matrix form of this solution also allows for recursive updates.

6.2 Under-Sampling and Optimal Under-Sampling

Under-sampling or non-baseband sampling is a technique where the sampling interval is larger than the Nyquist sampling interval. Traditionally, this type of sampling is discouraged because it tends to cause aliasing as well as cause aliased data to fold into unaliased data. However, if the band limits of the system are known, it is possible to prevent folding and use the aliased data directly. This dramatically cuts down on the number of data points needed and can dramatically increase the spectra update rate.

FIG. 22A shows a regularly sampled spectra with a 200 nm sampling interval taking about 700 samples total. This results in a 5 nm resolution at 850 nm. However, under-sampling around 850 nm, as shown in FIGS. 22B and 22C, yields 7.25 nm resolution for only 100 samples and 3.6 nm resolution for 100 samples. This can drastically reduce the sampling time while maintaining high resolutions.

Figure 23:
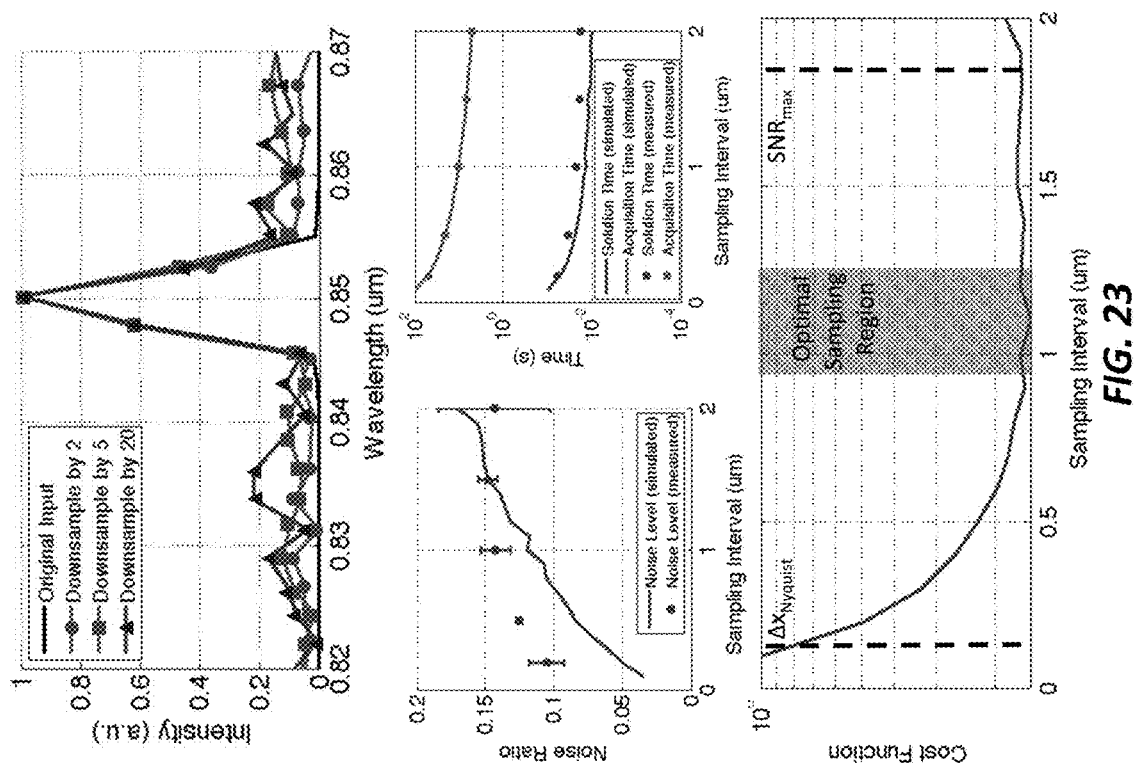
FIG. 23 illustrate a regime suitable for optimal under-sampling with an exemplary imaging spectrometer.

This information does not come for free, however. When more samples are taken, it is possible to reduce noise by averaging, which is inherently done through the least squares process. When under sampling is implemented, the reduction in the number of samples also reduces the averaging effect, thereby producing noisier spectra. Therefore, a cost function can be created to determine the optimal under-sampling interval for a given weight of importance of noise relative to sampling and computation time. In this case, the system is (artificially) restricted with constant spectral resolution with a constant set of desired spectral points. An "optimal" under-sampling interval can be determined using a cost function where the noise ratio $f(\Delta x)$, data acquisition time $g(\Delta x)$ and solution time $h(\Delta x)$ are considered with relative scaling constants $K_1$, $K_2$ and $K_3$. The sampling interval region is restricted by the Nyquist sampling rate, the maximum possible sampling rate, the maximum allowable sampling time, and the maximum allowable signal to noise ratio:

arg min $\Delta x K_1 f(\Delta x) + K_2 g(\Delta x) + K_3 h(\Delta x)$ subject to $\Delta x \in [\max(\Delta x_{Nyquist}, T_{max}), \min(\Delta x_{max}, SNR_{max})]$ Based on these criteria, simulation and experiments were performed to determine the optimal sampling region where the cost function is at a minimum. The sampling and computation times drop drastically with the decrease in the number of sampled points while the noise level increases slowly. FIG. 23 shows the optimal sampling region when the relative scaling of importance between time to noise is 5 to 1. Each simulation point is computed from 100 trials on data with white noise. For this set of parameters, the optimal sampling interval is around 1 μm, which is much greater than the Nyquist sampling rate for a laser at 850 nm.

6.3 Adaptive Under-Sampling and Non-Uniform Sampling

Non-uniform sampling includes algorithms such as multi-coset sampling and random sampling schemes. These schemes are used when some limited information about the spectral content is known. Random sampling can be done when the underlying spectra is sparse, meaning that most of the spectral content is zero except for a few areas which have very sharp peaks. Because of the sparsity of the data in the spectrum, it is possible to under-sample heavily, as described above. In order to do so without knowing the peak locations (which is not possible with simple under-sampling), the sampling interval should be uncorrelated to spread out the aliasing noise. This leads to random sampling schemes for sparse systems. This is the underlying basis for algorithms related to compressed sensing (such as the single pixel camera) and fast orthogonal search.

For systems that are not sparse, such as the case when white light or incoherent light from LEDs are used, the spectrometer may use an adaptive under-sampling algorithm. Adaptive under-sampling takes advantage of the fact that the act of obtaining more data points in the spectra automatically yields more spectral data. Since there is more data about the underlying spectrum, it is then possible to tailor the input to converge on the optimal, wider sampling interval over a single sampling sweep thereby producing the desired spectral resolution faster. For example, a controller implementing adaptive sampling may slowly increases the sampling interval as it learns more about the underlying spectra.

Figures 24A, 24B:
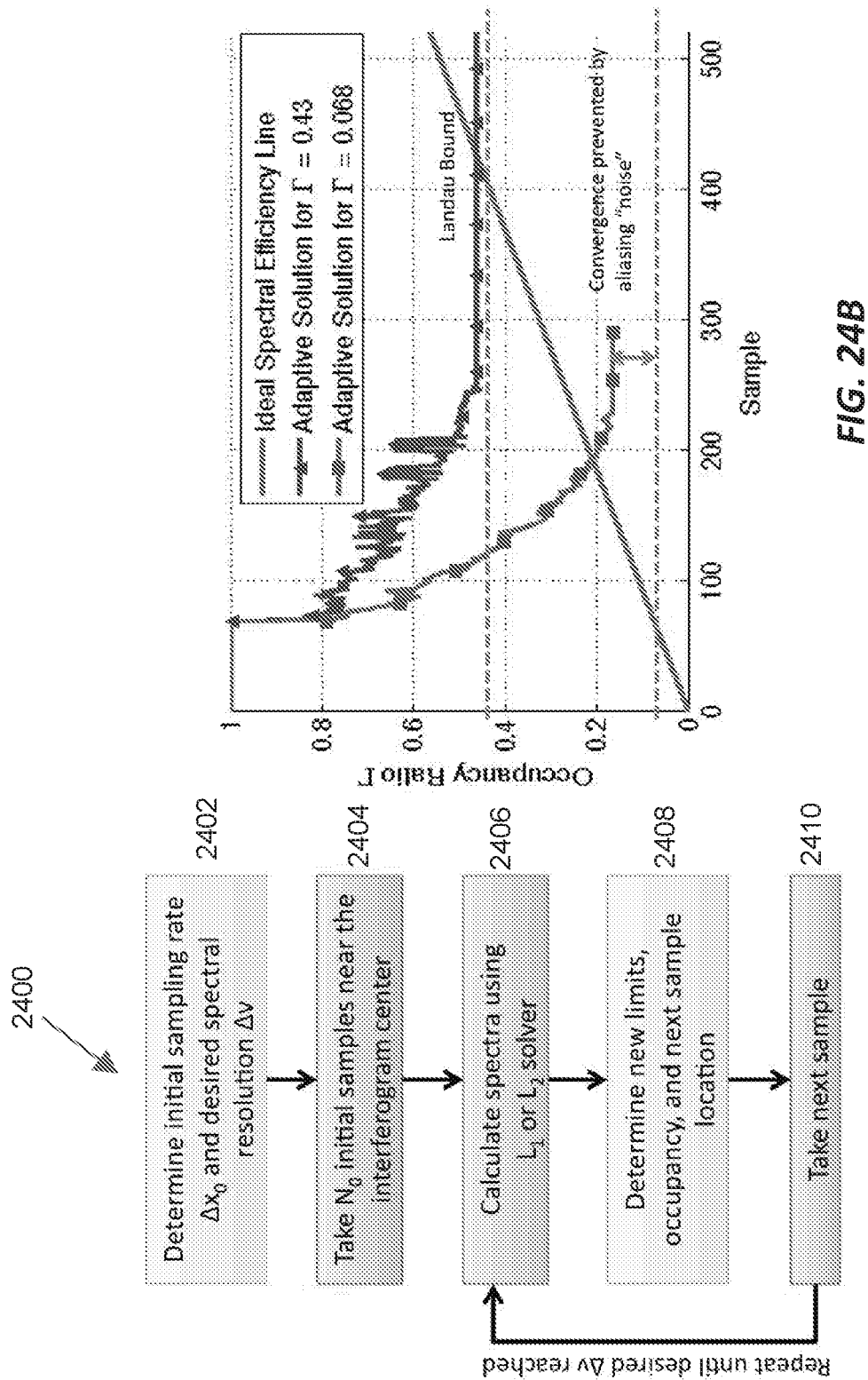
FIGS. 24A-24D illustrate an adaptive sampling process and its performance when implemented with an exemplary imaging spectrometer.

FIG. 24A is a flow diagram that illustrates adaptive sampling 2400. In step 2402, the controller determines the desired resolution and initial sampling rate which is related to the known band limits $\lambda_{max}$ and $\lambda_{min}$. This sampling rate is known as the Shannon non-baseband rate:

$$\Delta x_0 = \frac{1}{2} \lambda_{min} \left\lfloor \frac{\lambda_{max}}{\lambda_{max} - \lambda_{min}} \right\rfloor \text{ where}$$

$$x_i = x_{i-1} + \Delta x_0.$$

In step 2404, the spectrometer collects a small number of initial samples $N_0$ near the interferogram center. Once this is completed, the controller calculates low-resolution spectra using the solver described above (step 2406). When this result is obtained, the controller determines the band limits (locations in the spectra where information exists) and occupancy (ratio of occupied to total spectral data points) of the band of interest (step 2408). The controller uses this information to select the next sampling step with some relaxation term R:

$$\overline{\Delta x} \leq \frac{1}{2} \lambda_{min} \frac{\lambda_{occupied}}{\lambda_{total}} R \left\lfloor \frac{\lambda_{max}}{\lambda_{max} - \lambda_{min}} \right\rfloor \text{ where}$$

$$x_i = x_{i-1} + \Delta x_i.$$

Once the spectrometer acquires the next sample in step 2410, it recalculates the spectra using the algorithm outlined above and repeats the process until the desired resolution is achieved. Note that in an $L_2$ norm algorithm, the limits become smaller (only occupied parts of the spectra are set up in the calculation of $w_i$) because there might otherwise be not enough data to solve the problem. An $L_1$ norm algorithm might not have such a restriction but could run much slower. The shrinking limits in the exemplary algorithm make the $L_2$ norm solution feasible.

One consideration in the algorithm solution is how to convert the sampling step limitation $\overline{\Delta x}$ to a value $\Delta x$. There are several possible ways to do this such as choosing $\Delta x$ at random such that the average is $\overline{\Delta x}$. Another method is to choose $\Delta x = \overline{\Delta x}$. Other possible methods include multi-coset and other packing algorithms as well as direct constrained solutions that optimize the sampling point based on a guess of what the spectra looks like.

FIG. 24B shows how the occupancy ratio drops as more samples are taken for two different types of spectra. One is a relatively sparse spectrum (narrowband) with 6.8% occupancy and a spectrum with broadband spectral information with 43% occupancy. The spectra with less occupancy drops more quickly. Both types of spectra converge after reaching the Landau bound, which specifies that two data points must be obtained for each spectral point in order to cover both the sine and cosine phases of the solution algorithm.

Figures 24C, 24D:
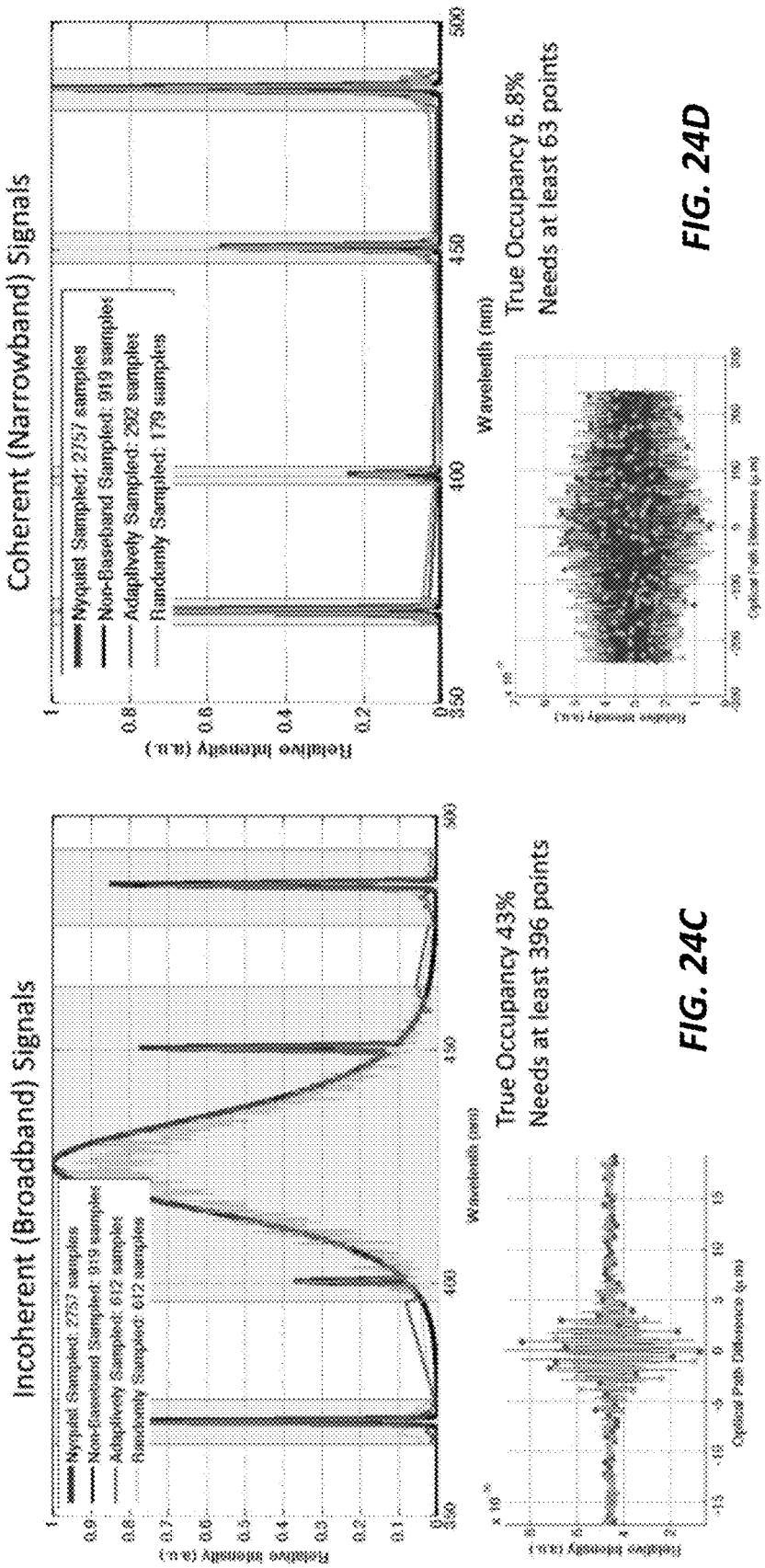

FIGS. 24C and 24D shows the spectrum and the sampled data for broadband and narrowband signals, respectively. For the broadband signal, adaptive sampling is much better than the Nyquist, non-baseband, and randomly sampling. It requires significantly fewer samples than both the Nyquist and non-baseband algorithms. When sampled adaptively, the spectrum was acquired with only 612 samples, which is only 22% of the total number of samples needed for Nyquist sampling. The adaptive sampled data is not as noisy as non-uniform randomly sampled data. Without being bound by any particular theory, adaptive sampling performs better than non-uniform random sampling because the initial sampling of $N_0$ data points and tighter sampling spacing near the center of the interferogram capture the incoherent data much better than random sampling.

For the narrowband signal, the adaptive sampling beats both traditional Nyquist sampling and non-baseband sampling. The sparse spectra required only 10.5% the total number of Nyquist samples. Random sampling can actually work faster than adaptive sampling because the initial investment of $N_0$ data points in adaptive sampling does not occur in the random algorithm, thereby allowing random sampling to identify the spectra faster. Overall, adaptive sampling is much more flexible in that it can handle broadband and narrowband spectra. Adaptive sampling also produces spectra as it learns more about the underlying system therefore allowing the spectrometer to confirm the shape of the spectrum over time. Without any prior knowledge, the spectrometer was able to terminate intelligently taking a very small number of samples for each spectrum. Additional tests show that adaptive sampling can be robust to noise by using the relaxation parameters causing the algorithm to take a few extra data points.

FIGS. 25A-25D shows the results of implementing adaptive sampling with an exemplary Fourier-transform imaging spectrometer. Three laser sources were used for this experiment at 532 nm, 850 nm, and 1064 nm. One pixel in the spectrometer camera detected the reference beam at 850 nm and three other pixels in the spectrometer camera sensed light at 532 nm and 1064 nm. The inset of FIG. 25A shows part of the full image from the imaging interferometer (from which the pixels are chosen). The data plotted in FIG. 25A were Nyquist sampled at an interval of 200 nm and took over 50 seconds to complete at 30 frames per second. The data shown in FIG. 25B were adaptively sampled and took less than 15 seconds to complete at 30 frames per second. The resulting spectrum has the same resolution as the Nyquist sampled spectrum. Due to the adaptive sampling settings, only occupied spectral bands are solved for and plotted. The peak data is slightly different due to experimental variation. FIG. 25C shows how the occupancy ratio decreases quickly and steadily to the occupancy bound and FIG. 25D shows the spectral acquisition time. Both Nyquist sampling and adaptive sampling stop at around the same position, which leads to both having the same spectral resolution. As the experiment shows, the adaptive sampling works well in practice.

6.4 Recursive Sampling

While adaptive sampling reduces the number of images necessary to produce a full spectral image, recursive sampling can be used to update the spectral information between full spectral images. For example, if 100 images taken at 2000 frames per second are required to create a single full spectral image, the full spectral image rate would be 10 full spectra per second. If a recursive sampling algorithm were used, it would be possible to make small updates the spectral image after each image; this allows the recursively sampled full spectral image rate to be as high as 2000 frames per second. This can be useful for pushing the spectral update to the user at faster rates. Possible applications could be video monitoring of changes in biological fluorescence to changes during chemical mixing causing changes in the Raman spectra. Changes in blood oxygen content of an entire image as a function of heart rate could also be monitored in this fashion.

In order to implement recursive sampling, the underlying model should not change (the size of the spectra of interest m=1 . . . M and the locations of $w_i$) that the spectral resolution and sampling range are fixed (unlike the adaptive sampling algorithm). Recursive sampling tends to have a fast update rate (short calculation times) and can be used to decrease noise by obtaining more samples.

One limitation of recursive sampling is that the intermediate spectral updates may not track fast changes and may have a "time constant" on the order of the number of samples acquired for a full spectra. Therefore, the true update speed may be limited by the spectral resolution and range. Recursive sampling works well for both narrowband (coherent) and broadband (incoherent) signals.

For recursive sampling, the model relation is, Y=PA+E. Defining two variables, $\Phi(n)=P^TP$ and $\Psi(n)=P^TY$, makes it possible to derive update equations for a single data point update using the recursive least squares algorithm, $$K(n) = \frac{\lambda^{-1}\Phi^{-1}(n-1)P_m^T(n)}{1+\lambda^{-1}P_m(n)\Phi^{-1}(n-1)P_m^T(n)},$$

$$\Phi^{-1}(n) = \lambda^{-1}\Phi^{-1}(n-1) - \lambda^{-1}K(n)P_m(n)\Phi^{-1}(n-1),$$

$$\hat{A}(n) = \hat{A}(n-1) + \Phi^{-1}(n)P_m^T(n)\left[Y(n) - P_m(n)\hat{A}(n-1)\right].$$

At the current iteration n, the A(n) vector is used to obtain the desired magnitude and phase. The parameter $\lambda$, is a forgetting factor where $\lambda=1$ means that no past information is forgotten. Due to the recursive nature of recursive sampling, a full matrix inversion is not required to update the full spectrum and the spectrum can be updated quickly. To initialize recursive sampling, a guess can be made of the spectrum or a full spectral image can be obtained.

The update equations above are suitable for updates after each image g=1. But it can be desirable to update the spectrum after acquiring a few data points g>1 since the spectra updates slowly and updates for g=1 may be in the noise. For $g\geq 1$, define:

$$F = [\,P_m(n-g+1) \quad P_m(n-g+2) \quad \ldots \quad P_m(n)\,],$$

$$G = \left[\,\lambda^{\frac{g-1}{2}}P_m(n-g+1) \quad \lambda^{\frac{g-1}{2}}P_m(n-g+1) \quad \ldots \quad P_m(n)\,\right], \text{ and}$$

$$H = [\,\lambda^{g-1}P_m(n-g+1) \quad \lambda^{g-2}P_m(n-g+2) \quad \ldots \quad P_m(n)\,].$$

The update equations are therefore, $$K = \lambda^{-g}\Phi^{-1}(n-g)G^T[I+\lambda^{-g}G\Phi^{-1}(n-g)G^T],$$

$$\Phi^{-1}(n) = \lambda^{-g}\Phi^{-1}(n-g) - \lambda^{-g}KG\Phi^{-1}(n-g), \text{ and}$$

$$\hat{A}(n) = \hat{A}(n-1) + \Phi^{-1}(n)H^T\left[Y - F\hat{A}(n-1)\right].$$

Figure 26A:
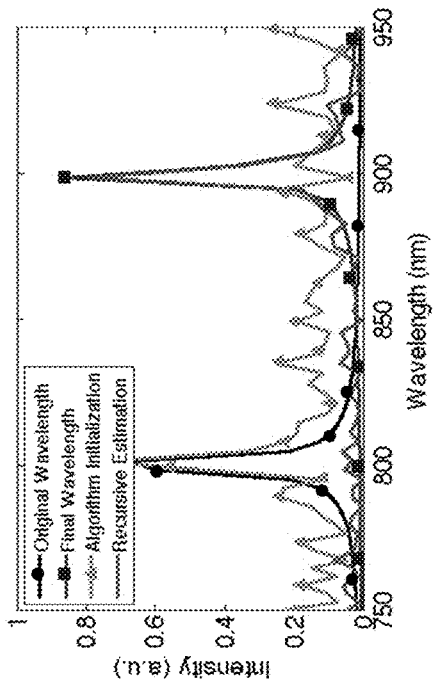
FIGS. 26A-26D are plots illustrating the recursive sampling with an exemplary imaging spectrometer.
Figure 26B:
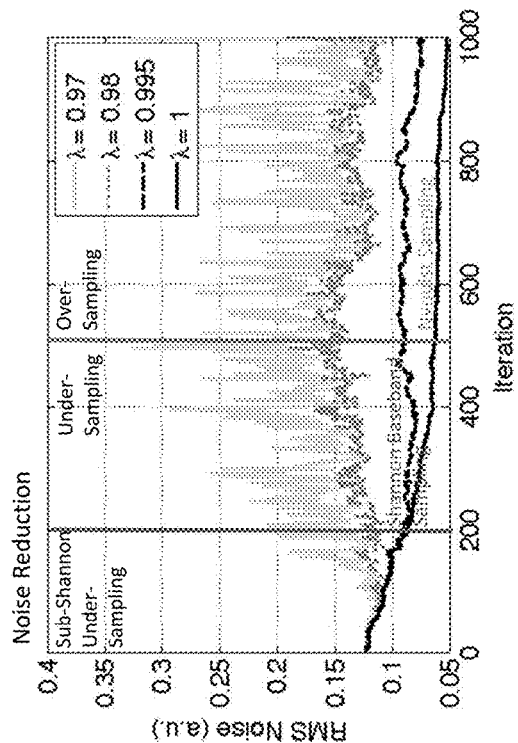
Figure 26C:
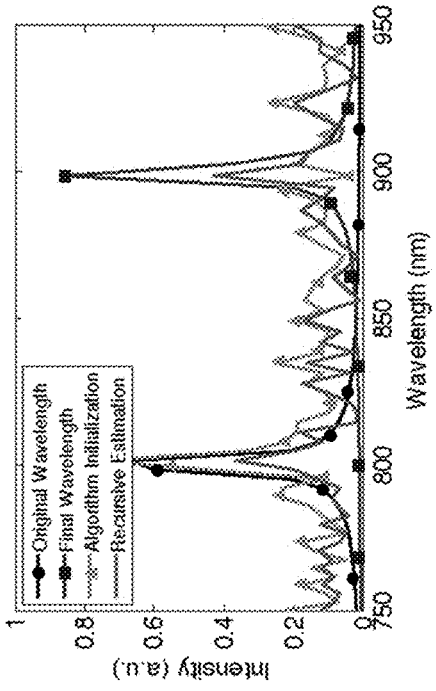
Figure 26D:
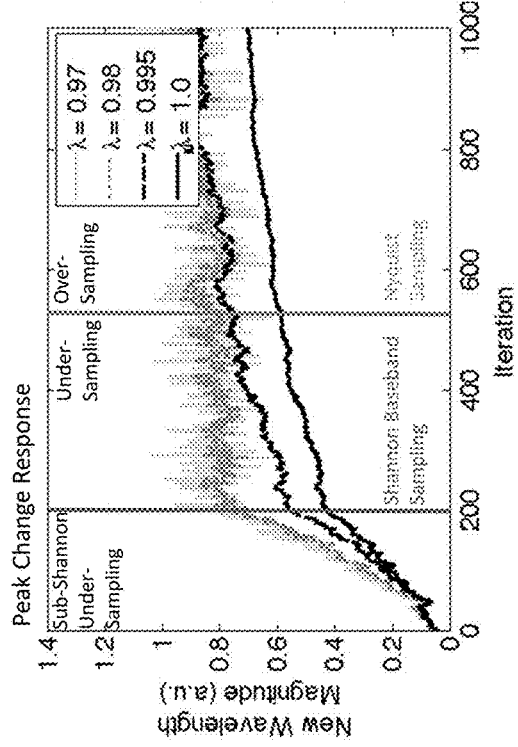

FIGS. 26A-26D show simulations of recursive sampling starting with an under-sampled spectrum where 200 samples are taken to cover the spectral range between 750 nm and 950 nm. In FIG. 26A (for $\lambda=1$, g=1), the original spectral information (circles) is shown and is used to initialize the algorithm (triangles). At iteration 1, the spectra changes instantaneously to the new spectrum (squares) and the result at update iteration 200 is shown (line). The recursive estimation has slowly updating and by iteration 4000, has fully converged to the new spectrum. FIG. 26C shows how the peak at 900 nm changes as a function of iteration for different forgetting factors. The lower the forgetting factor, the faster the adaptation and the larger the noise. For a forgetting factor of 1, the adaptation is slow but the RMS noise as a function of iteration drops to lower levels as shown in FIG. 26D. Lower forgetting factors can speed up adaptation but reduces the ability to reject noise. A spectrometer executing recursive sampling can clearly sense changes in the spectra at sub-Shannon sampling intervals.

For the case where the forgetting factor is large, oversampling the spectrum can clearly reduce noise.

Figure 27:
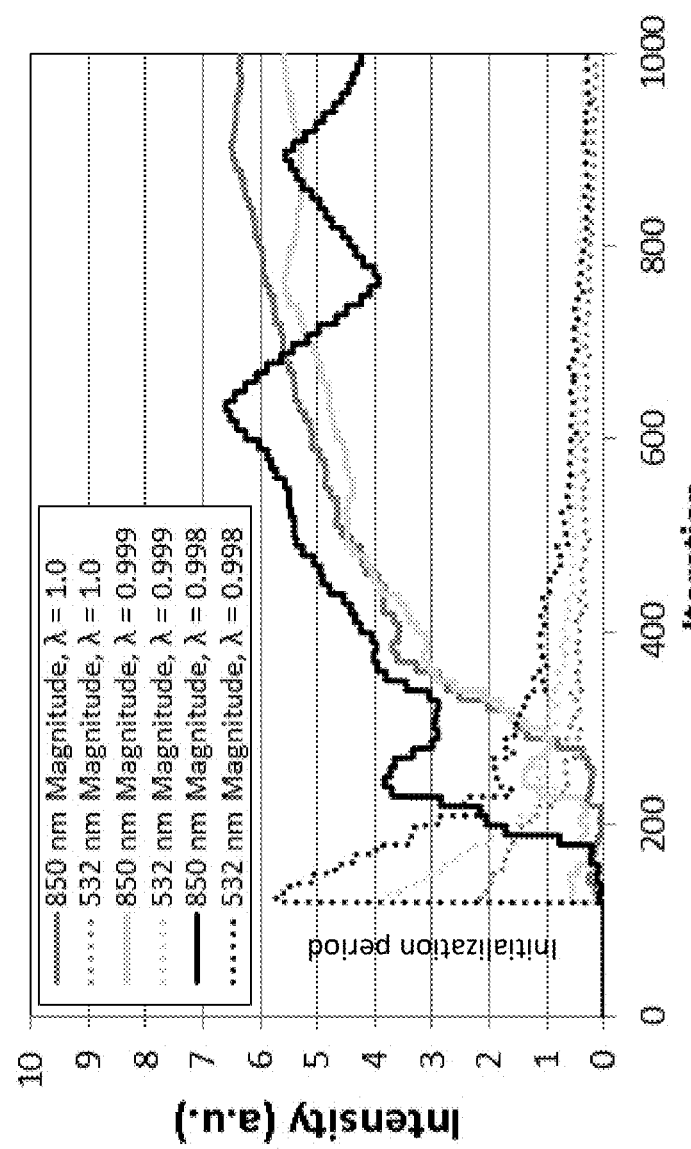
FIG. 27 is a plot of intensity versus iteration number for recursive sampling of a scene with an exemplary imaging spectrometer.

FIG. 27 shows the experimental results of an experiment where g=10 and the number of images used for a full spectra is 100 samples. A 532 nm laser is turned off quickly followed by a 850 nm laser that is turned on. For $\lambda=1$, there is less oscillation but the data updates more slowly, increasing the settling time. If this spectral data had been more traditionally updated, e.g., for the whole period of 1000 iterations, only 10 full spectral updates would have been completed since the number of images per spectra is 100. However, by using recursive sampling, the spectrometer can acquire at least 90 to 900 spectra over the same period. This greatly increases the sensitivity of the spectral update to the user.

7.0 Additional Applications

There are many synergies between the imaging and the spectral acquisition components. Tilting the mirror slightly yields extra position offsets for every image captured (each pixel is at a different position offset). If the image covers areas that have the same spectral information, the data collected from these areas can be combined thereby decreasing the noise of the spectra and further reducing the number of images or data positions that have to be sampled. Image tracking methods can be combined with the adaptive sampling algorithm so that if the image moves slightly during an acquisition, the full spectra does not need to be obtained but can be mapped with the original data obtained before the disturbance. This may improve the acquisition process.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system for imaging spectroscopy of an object, the system comprising:
   an interferometer, in optical communication with the object, to delay a first portion of an object beam from the object with respect to a second portion of the object beam by a delay period, the delay period proportional to an optical path length difference defined by a first optical element and a second optical element;
   a first detector array, in optical communication with the interferometer, to sense at least one object interference pattern between the first portion of the object beam and the second portion of the object beam, the at least one object interference pattern representing a spectroscopic image of at least a portion of the object;
   a reference beam source, in optical communication with the interferometer, to illuminate the first optical element with a first portion of a reference beam and the second optical element with a second portion of the reference beam; and
   a second detector array, in optical communication with the interferometer, to sense a reference interference pattern between the first portion of the reference beam and the second portion of the reference beam, the reference interference pattern representing a position of the first optical element with respect to the second optical element.

2. The system of claim 1, further comprising:
   a controller, operably coupled to the second detector array, to determine a misalignment of the first optical element with respect to the second optical element based at least in part on the reference interference pattern; and at least one actuator, in mechanical communication with the first optical element, to move the first optical element with respect to the second optical element in response to the misalignment determined by the controller.

3. The system of claim 2, wherein the at least one actuator is configured to translate, tip, and/or tilt the first optical element with respect to the second optical element in response to the misalignment.

4. The system of claim 2, wherein the controller is configured to determine the optical path length difference based at least in part on the reference interference pattern and to actuate the at least one actuator so as to vary the optical path length difference.

5. The system of claim 2, wherein:
the at least one actuator is configured to move the first optical element to a plurality of positions with respect to the second optical element, each position in the plurality of positions corresponding to a different optical path length difference; and
the first detector array is configured to sense a plurality of object interference patterns, each object interference pattern in the plurality of object interference patterns corresponding to a respective position in the plurality of positions.

6. The system of claim 5, wherein the controller is configured to select at least one first position within the plurality of positions in response to at least one object interference pattern in the plurality of object interference patterns.

7. The system of claim 5, further comprising:
a processor, operably coupled to the first detector array and the controller, to estimate a spectroscopic image of the object based on the plurality of object interference patterns, and
wherein the controller is configured to select at least one position within the plurality of positions based at least in part on the spectroscopic image.

8. The system of claim 5, wherein the plurality of positions includes fewer positions than a number of resolvable spectral bins in the spectroscopic image.

9. The system of claim 5, wherein the controller is configured to control the at least one actuator based at least in part on a transfer function of the at least one actuator and a desired position of the first optical element with respect to the second optical element.

10. The system of claim 2, wherein the at least one actuator comprises:
a voice-coil element to move the first optical element with respect to the second optical element.

11. The system of claim 10, wherein the at least one actuator further comprises:
a piezo-electric element to move the first optical element with respect to the second optical element at a rate greater than a frame rate of the first detector array and smaller than bandwidth of the second detector array.

12. The system of claim 2, further comprising:
at least one flexure coupling the at least one actuator to the first optical element.

13. The system of claim 1, further comprising:
a frame to support the first optical element and the second optical element; and
at least one flexure coupling the first optical element to the frame.

14. The system of claim 1, further comprising:
a light source to illuminate an object so as to produce the object beam via reflection, scattering, and/or emission by the object.

15. The system of claim 14, further comprising:
an endoscopic housing to contain the light source, the reference beam source, the first optical element, and the second optical element.

16. The system of claim 1, wherein the first portion of the object beam illuminates the first optical element and the second portion of the object beam illuminates the second optical element.

17. A method of imaging spectroscopy, the method comprising:
(A) receiving an object beam from an object;
(B) delaying, with an interferometer including a first optical element and a second optical element, a first portion of the object beam with respect to a second portion of the object beam by a delay period, the delay period proportional to an optical path length difference defined by the first optical element and the second optical element;
(C) sensing, with a first detector array, at least one object interference pattern between the first portion of the object beam and the second portion of the object beam, the at least one object interference pattern representing a spectroscopic image of at least a portion of the object;
(D) illuminating the first optical element with a first portion of a reference beam and the second optical element with a second portion of the reference beam; and
(E) sensing a reference interference pattern between the first portion of the reference beam and the second portion of the reference beam, the reference interference pattern representing a position of the first optical element with respect to the second optical element.

18. The method of claim 17, further comprising:
(F) determining, with a controller, a misalignment of the first optical element with respect to the second optical element based at least in part on the reference interference pattern; and
(G) moving, with at least one actuator, the first optical element with respect to the second optical element in response to the misalignment determined by the controller.

19. The method of claim 18, wherein (G) comprises translating, tipping, and/or tilting the first optical element with respect to the second optical element.

20. The method of claim 18, wherein (G) comprising actuating the at least one actuator based at least in part on a transfer function of the at least one actuator and a desired position of the first optical element with respect to the second optical element.

21. The method of claim 18, further comprising:
determining the optical path length difference based at least in part on the reference interference pattern; and
actuating the at least one actuator so as to vary the optical path length difference.

22. The method of claim 17, wherein:
(B) comprises delaying the first portion of the object beam with respect to the second portion of the object at each of a plurality of delay periods, and
(C) comprises sensing a plurality of object interference patterns corresponding to the plurality of delay periods.

23. The method of claim 22, wherein (B) comprises selecting at least one delay period in the plurality of delay periods in response to at least one object interference pattern in the plurality of object interference patterns.

24. The method of claim 22, wherein:
(C) further comprises estimating the spectroscopic image of the object based on the plurality of object interference patterns, and
(B) further comprises selecting at least one position within the plurality of positions based at least in part on the spectroscopic image.

25. The method of claim 24, wherein (C) further comprises estimating at least n spectral bins associated with the spectroscopic image from m object interference patterns, wherein n>m.

26. An imaging spectrometer comprising:
a beamsplitter, to split light from an object into a first object beam and a second object beam;
at least one optical element, in optical communication with the beamsplitter, to delay the first object beam with respect to the second object beam by a plurality of delay periods;
at least one actuator, in mechanical communication with the at least one optical element, to move the at least one optical element to each of a plurality of positions so as to produce the plurality of delay periods, the at least one actuator being further configured to tip and/or tilt the at least one optical element;
a detector array, in optical communication with the at least one optical element, to sense a plurality of interference periods, the plurality of interference periods comprising at least one interference pattern between the first object beam and the second object beam at each delay period in the plurality of delay periods; and
a processor, operably coupled to the detector array, to determine a spectroscopic image of the object based at least in part on the plurality of interference patterns and to determine at least one position in the plurality of positions based at least in part on the spectroscopic image and a transfer function of the at least one actuator.

27. The imaging spectrometer of claim 26, wherein the delay periods in the plurality of delay periods are spaced at irregular intervals.

* * * * *